United States Patent
Baumann et al.

(10) Patent No.: US 6,372,693 B1
(45) Date of Patent: Apr. 16, 2002

(54) SUBSTITUTED 2-(3-ALKENYL-BENZOYL)-CYCLOHEXANE-1,3-DIONES

(75) Inventors: Ernst Baumann, Dudenhofen; Wolfgang von Deyn, Neustadt; Stefan Engel, Idstein; Regina Luise Hill, Speyer; Uwe Kardorff, Mannheim; Guido Mayer, Neustadt; Martina Otten, Ludwigshafen; Michael Rack, Heidelberg; Joachim Rheinheimer; Matthias Witschel, both of Ludwigshafen; Karl-Otto Westphalen, Speyer; Ulf Misslitz, Neustadt; Helmut Walter, Obrigheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/423,117

(22) PCT Filed: Apr. 24, 1998

(86) PCT No.: PCT/EP98/02447

§ 371 Date: Nov. 2, 1999

§ 102(e) Date: Nov. 2, 1999

(87) PCT Pub. No.: WO98/50337

PCT Pub. Date: Nov. 12, 1998

(30) Foreign Application Priority Data

May 7, 1997 (DE) .......................... 197 19 380

(51) Int. Cl.$^7$ .................. A01N 35/00; C07C 255/07; C07C 49/23; C07D 239/00; C07D 211/70; C07D 263/02; C07D 333/02

(52) U.S. Cl. .................. 504/348; 504/130; 504/131; 504/136; 504/137; 504/139; 504/141; 504/189; 504/349; 504/350; 558/415; 558/416; 568/314; 568/319; 568/322; 568/329; 568/331; 544/242; 546/341; 546/351; 546/352; 548/215; 548/341.5; 548/373.1; 549/29; 549/80; 549/369; 549/506

(58) Field of Search ........................ 558/416, 415; 568/314, 319, 322, 329, 331; 544/242; 546/351, 352; 548/215, 341.5, 373.1; 549/29, 80, 369, 506; 504/130, 131, 136, 137, 139, 140, 141, 189, 348, 349, 350

(56) References Cited

U.S. PATENT DOCUMENTS

| | | | |
|---|---|---|---|
| 4,652,303 A | 3/1987 | Watson et al. ............ 71/88 |
| 4,749,687 A | 6/1988 | Bindra et al. ............ 514/18 |
| 4,822,906 A | 4/1989 | Carter ..................... 558/416 |
| 4,946,981 A | 8/1990 | Carter et al. ............. 558/415 |
| 4,997,473 A | 3/1991 | Nguyen ................... 71/98 |

FOREIGN PATENT DOCUMENTS

| | | |
|---|---|---|
| CA | 2151498 | 6/1994 |
| EP | 135191 | 3/1985 |
| EP | 137963 | 4/1985 |
| EP | 319075 | 6/1989 |
| WO | 93/24446 | 12/1993 |

Primary Examiner—Sreeni Padmanabhan
(74) Attorney, Agent, or Firm—Keil & Weinkauf

(57) ABSTRACT

The invention relates to 2-(3-alkenylbenzoyl)cyclohexane-1,3-diones of the formula I

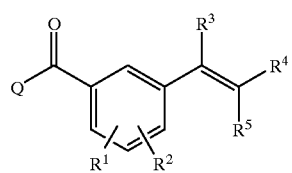

where the variables have the following meanings:

$R^1$, $R^2$ are hydrogen, nitro, halogen, cyano, thiocyanato, alkyl, haloalkyl, alkoxyalkyl, alkenyl, alkynyl, —$OR^6$, —$OCOR^7$, —$OSO_2R^7$, —SH, —$S(O)_nR^8$, —$SO_2OR^6$, —$SO_2NR^6R^9$, —$NR^9SO_2R^7$ or —$NR^9COR^7$;

$R^3$ is hydrogen, halogen, alkyl, haloalkyl, alkoxy, alkenyl, alkynyl;

$R^4$, $R^5$ are hydrogen, nitro, halogen, cyano, thiocyanato, alkyl, haloalkyl, cycloalkyl, alkenyl, cycloalkenyl, alkynyl, alkoxy, alkylthio, haloalkoxy, —$COR^{10}$, —$CO_2R^{10}$, —$COSR^{10}$, —$CONR^{10}R^{11}$, —$C(R^{12})$ =$NR^{13}$, —$PO(OR^{10})(OR^{11})$; unsubstituted or substituted alkyl, heterocyclyl, heterocyclylalkyl, phenyl, phenylalkyl, hetaryl or hetarylalkyl; or $R^4$ and $R^5$ together form an alkanediyl chain which can be substituted and/or can be interrupted by a hetero atom;

Q is an unsubstituted or substituted cyclohexane-1,3-dione ring which is linked in the 2-position;

and agriculturally useful salts thereof;

processes for the preparation of the compounds of the formula I; compositions comprising them; and the use of these derivatives or compositions comprising them for controlling undesired plants.

9 Claims, No Drawings

SUBSTITUTED 2-(3-ALKENYL-BENZOYL)-CYCLOHEXANE-1,3-DIONES

This Application is a 371 of PCT/EP98/02447 filed Apr. 24, 1998.

The present invention relates to 2-(3-alkenylbenzoyl) cyclohexane-1,3-diones of the formula I

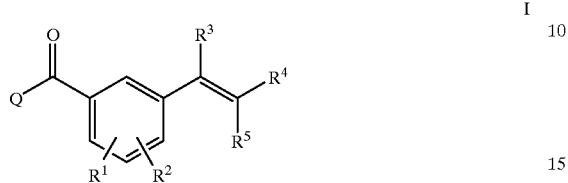

where the variables have the following meanings:

$R^1$, $R^2$ are hydrogen, nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^6$, —$OCOR^7$, —$OSO_2R^7$, —SH, —$S(O)_nR^8$, —$SO_2OR^6$, —$SO_2NR^6R^9$, —$NR^9SO_2R^7$ or —$NR^9COR^7$;

$R^3$ is hydrogen, halogen, $C_1$–$C_6$-alkyl, $C_1$–$C_6$-haloalkyl, $C_1$–$C_6$-alkoxy, $C_2$–$C_6$-alkenyl, $C_2$–$C_6$-alkynyl;

$R^4$, $R^5$ are hydrogen, nitro, halogen, cyano, thiocyanato, $C_1$–$C_6$-alkyl, $C_1$–$C_6$-haloalkyl, $C_3$–$C_6$-cycloalkyl, $C_2$–$C_6$-alkenyl, $C_4$–$C_6$-cycloalkenyl, $C_2$–$C_6$-alkynyl, $C_1$–$C_6$-alkoxy, $C_1$–$C_6$-alkylthio, $C_1$–$C_6$-haloalkoxy, —$COR^{10}$, —$CO_2R^{10}$, —$COSR^{10}$, —$CONR^{10}R^{11}$, —$C(R^{12})$=$NR^{13}$, —$PO(OR^{10})(OR^{11})$, $C_1$–$C_4$-alkyl which has attached to it a radical from amongst the following group: hydroxyl, —$COR^{10}$, —$CO_2R^{10}$, —$COSR^{10}$, —$CONR^{10}R^{11}$ or —$C(R^{12})$=$NR^{13}$; heterocyclyl, heterocyclyl-$C_1$–$C_4$-alkyl, phenyl, phenyl-$C_1$–$C_4$-alkyl, hetaryl, hetaryl-$C_1$–$C_4$-alkyl, it being possible for the six last-mentioned radicals to be substituted; or $R^4$ and $R^5$ together form a $C_2$–$C_6$-alkanediyl chain which can be mono- to tetrasubstituted by $C_1$–$C_4$-alkyl and/or can be interrupted by oxygen or sulfur or by a nitrogen which is unsubstituted or substituted by $C_1$–$C_4$-alkyl;

n is 0, 1 or 2;

$R^6$ is hydrogen, $C_1$–$C_6$-alkyl, $C_1$–$C_6$-haloalkyl, $C_1$–$C_6$-alkoxy-$C_2$–$C_6$-alkyl, $C_3$–$C_6$-alkenyl or $C_3$–$C_6$-alkynyl;

$R^7$ is $C_1$–$C_6$-alkyl or $C_1$–$C_6$-haloalkyl;

$R^8$ is $C_1$–$C_6$-alkyl, $C_1$–$C_6$-haloalkyl, $C_1$–$C_6$-alkoxy-$C_2$–$C_6$-alkyl, $C_3$–$C_6$-alkenyl or $C_3$–$C_6$-alkynyl;

$R^9$ is hydrogen or $C_1$–$C_6$-alkyl;

$R^{10}$ is hydrogen, $C_1$–$C_6$-alkyl, $C_3$–$C_6$-cycloalkyl, $C_1$–$C_6$-haloalkyl, $C_3$–$C_6$-alkenyl, $C_3$–$C_6$-alkynyl, phenyl or benzyl, it being possible for the two last-mentioned radicals to be partially or fully halogenated and/or to have attached to them one to three radicals from amongst the following group: nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylcarbonyl or $C_1$–$C_4$-alkoxycarbonyl;

$R^{11}$ is hydrogen, $C_1$–$C_6$-alkyl, $C_3$–$C_6$-alkenyl or $C_3$–$C_6$-alkynyl; or $R^{10}$ and $R^{11}$ together form a $C_2$–$C_6$-alkanediyl chain which can be mono- to tetrasubstituted by $C_1$–$C_4$-alkyl and/or can be interrupted by oxygen or sulfur or by a nitrogen which is unsubstituted or substituted by $C_1$–$C_4$-alkyl;

$R^{12}$ is hydrogen, $C_1$–$C_6$-alkyl, $C_1$–$C_6$-haloalkyl, $C_1$–$C_6$-alkoxy, $C_1$–$C_6$-alkoxycarbonyl, $C_3$–$C_6$-cycloalkyl, $C_2$–$C_6$-alkenyl, $C_2$–$C_6$-alkynyl, phenyl or benzyl, it being possible for the two last-mentioned radicals to be partially or fully halogenated and/or to have attached to them one to three radicals from amongst the following group: nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylcarbonyl or $C_1$–$C_4$-alkoxycarbonyl;

$R^{13}$ is $C_1$–$C_6$-alkyl, $C_1$–$C_6$-haloalkyl, $C_3$–$C_6$-cycloalkyl, $C_3$–$C_6$-alkenyl, $C_3$—$C_6$-alkynyl, $C_1$–$C_6$-alkoxy, $C_1$–$C_6$-haloalkoxy, $C_3$–$C_6$-cycloalkyloxy, $C_3$–$C_6$-alkenyloxy, $C_3$–$C_6$-alkynyloxy, phenyl, benzyl or phenyl-$C_1$–$C_4$-alkoxy, it being possible for the three last-mentioned radicals to be partially or fully halogenated and/or to have attached to them one to three radicals from amongst the following group:
  nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylcarbonyl or $C_1$–$C_4$-alkoxycarbonyl;

Q is an unsubstituted or substituted cyclohexane-1,3-dione ring which is linked in the 2-position;

and to agriculturally useful salts thereof.

The invention furthermore relates to processes for the preparation of compounds of the formula I, to compositions comprising them, and to the use of the compounds of the formula I and to compositions comprising them for controlling harmful plants.

WO 93/24446 discloses cyclohexane-1,3-diones which are substituted in the 2-position and which have anthelminthic and nematicidal properties. 2-Benzoylcyclohexane-1, 3-diones are also known from the literature, for example from EP-A 135 191, EP-A 137 963 and EP-A 319 075. However, the herbicidal properties of these compounds and their crop plant tolerance are only moderately satisfactory.

It is an object of the present invention to find, in particular, herbicidally active compounds which have improved properties.

We have found that this object is achieved by the 2-(3-alkenylbenzoyl)cyclohexane-1,3-diones of the formula I and their herbicidal action.

We have furthermore found highly active herbicidal compositions which comprise the compounds I. In addition, we have found processes for the preparation of these compositions and methods of controlling undesired vegetation using the compounds I.

The present invention also relates to stereoisomers of the compounds of the formula I. This embraces not only pure stereoisomers, but also mixtures of these.

The compounds of the formula I contain a carbon-carbon double bond and are therefore present in the form of E isomers or Z isomers or E/Z; isomer mixtures. Furthermore, the compounds of the formula I can contain other carbon-carbon or carbon-nitrogen double bonds. The invention relates not only to the pure geometric isomers, but also to mixtures of these.

Equally, the compounds of the formula I can have one or more chiral centers, depending on the substitution pattern, in which case they exist as enantiomer or diastereomer mixtures. The invention relates not only to the pure enantiomers or diastereomers, but also to mixtures of these.

The compounds of the formula I can also exist in the form of their agriculturally useful salts, the type of salt generally being of no importance. In general, the salts of those cations or the acid addition salts of those acids are suitable whose cations, or anions, do not adversely affect the herbicidal action of the compounds I.

Cations which are suitable are, in particular, ions of the alkali metals, preferably lithium, sodium and potassium, of the alkaline earth metals, preferably calcium and magnesium, and of the transition metals, preferably manganese, copper, zink and iron, and also ammonium, it being possible in this case, if desired, for one to four hydrogen atoms to be replaced by $C_1$–$C_4$-alkyl, hydroxy-$C_1$–$C_4$-alkyl, $C_1$–$C_4$-alkoxy-$C_1$–$C_4$-alkyl, hydroxy-$C_1$–$C_4$-alkoxy-$C_1$–$C_4$-alkyl, phenyl or benzyl, preferably ammonium, dimethylammonium, diisopropylammonium, tetramethylammonium, tetrabutylammonium, 2-(2-hydroxyeth-1-oxy)eth-1-ylammonium, di-(2-hydroxyeth-1-yl)ammonium, trimethylbenzylammonium furthermore phosphonium ions, sulfonium ions, preferably tri($C_1$–$C_4$-alkyl)sulfonium and sulfoxonium ions, preferably tri ($C_1$–$C_4$-alkyl)sulfoxonium.

Anions of useful acid addition salts are mainly chloride, bromide, fluoride, hydrogen sulfate, sulfate, dihydrogen phosphate, hydrogen phosphate, nitrate, hydrogen carbonate, carbonate, hexafluorosilicate, hexafluorophosphate, benzoate and the anions of $C_1$–$C_4$-alkanoic acids, preferably formate, acetate, propionate and butyrate.

Mention must be made of the compounds of the formula I according to the invention where the variable Q is a cyclohexane-1,3-dione ring of the formula II

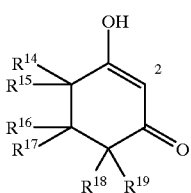

II which is linked in the 2-position, II also representing the tautomeric formulae II' and II"

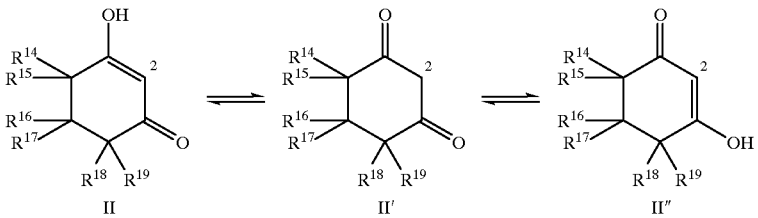

where
$R^{14}$, $R^{15}$, $R^{17}$ and $R^{19}$ are hydrogen or $C_1$–$C_4$-alkyl;
$R^{16}$ is hydrogen, $C_1$–$C_4$-alkyl, $C_1$–$C_4$-haloalkyl or $C_3$–$C_4$-cycloalkyl, it being possible for the three last-mentioned groups to have attached to them one to three of the following substituents: $C_1$–$C_4$-alkylthio or $C_1$–$C_4$-alkoxy; or
is tetrahydropyran-2-yl, tetrahydropyran-3-yl, tetrahydropyran-4-yl, tetrahydrothiopyran-2-yl, tetrahydrothiopyran-3-yl, tetrahydrothiopyran-4-yl, 1,3-dioxolan-2-yl, 1,3-dioxan-2-yl, 1,3-oxathiolan-2-yl, 1,3-oxathian-2-yl, 1,3-dithiolan-2-yl or 1,3-dithian-2-yl, it being possible for the 6 last-mentioned radicals to be substituted by one to three $C_1$–$C_4$-alkyl radicals;
$R^{18}$ is hydrogen, $C_1$–$C_4$-alkyl or $C_1$–$C_6$-alkoxycarbonyl; or $R^{16}$ and $R^{19}$ together form a π bond or a three- to six-membered carbocyclic ring; or
the $CR^{16}R^{17}$ unit may be replaced by C=O.

The organic moieties mentioned for the substituents $R^1$–$R^{19}$ or as radicals on phenyl, hetaryl and heterocyclyl rings represent collective terms for individual enumerations of the individual group members. All hydrocarbon chains, ie. all alkyl, haloalkyl, cycloalkyl, alkoxyalkyl, alkoxy, haloalkoxy, cycloalkoxy, alkylthio, alkylcarbonyl, alkoxycarbonyl, alkenyl, cycloalkenyl, alkynyl, alkenyloxy, alkynyloxy moieties can be straight-chain or branched. Unless otherwise specified, halogenated substituents preferably have attached to them one to five identical or different halogen atoms. Halogen means in each case fluorine, chlorine, bromine or iodine.

Examples of other meanings are:
$C_2$–$C_4$-alkyl: ethyl, n-propyl, 1-methylethyl, butyl, 1-methylpropyl, 2-methylpropyl or 1,1-dimethylethyl;
$C_1$–$C_4$-alkyl and the alkyl moieties of $C_1$–$C_4$-alkoxy-$C_1$–$C_4$-alkyl, hydroxy-$C_1$–$C_4$-alkoxy-$C_1$–$C_4$-alkyl, $C_1$–$C_4$-alkylcarbonyl, heterocyclyl-$C_1$–$C_4$-alkyl, phenyl-$C_1$–$C_4$-alkyl, hetaryl-$C_1$–$C_4$-alkyl: $C_2$–$C_4$-alkyl as mentioned above, and also methyl;
$C_2$–$C_6$-alkyl and the alkyl moieties of $C_1$–$C_6$-alkoxy-$C_2$–$C_6$-alkyl: $C_2$–$C_4$-alkyl as mentioned above, and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl or 1-ethyl-3-methylpropyl;
$C_1$–$C_6$-alkyl and the alkyl moieties of $C_1$–$C_6$-alkoxy-$C_1$–$C_6$-alkyl: $C_2$–$C_6$-alkyl as mentioned above, and also methyl;
$C_1$–$C_4$-haloalkyl: a $C_1$–$C_4$-alkyl radical as mentioned above which is partially or fully substituted by fluorine, chlorine, bromine and/or iodine, eg. chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl;

$C_1$–$C_6$-haloalkyl: $C_1$–$C_4$-haloalkyl as mentioned above, and also 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl or dodecafluorohexyl;

$C_1$–$C_4$-alkoxy and the alkoxy moieties of $C_1$–$C_4$-alkoxy-$C_1$–$C_4$-alkyl, hydroxy-$C_1$–$C_4$-alkoxy-$C_1$–$C_4$-alkyl and $C_1$–$C_4$-alkoxycarbonyl: methoxy, ethoxy, propoxy, 1-methylethoxy, butoxy, 1-methylpropoxy, 2-methylpropoxy or 1,1-dimethylethoxy;

$C_1$–$C_6$-alkoxy and the alkoxy moieties of $C_1$–$C_6$-alkoxy-$C_1$–$C_6$-alkyl and $C_1$–$C_6$-alkoxycarbonyl: $C_1$–$C_4$-alkoxy as mentioned above, and also pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy;

$C_1$–$C_4$-haloalkoxy: a $C_1$–$C_4$-alkoxy radical as mentioned above which is partially or fully substituted by fluorine, chlorine, bromine and/or iodine, eg. fluoromethoxy, difluoromethoxy, trifluoromethoxy, chlorodifluoromethoxy, bromodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or nonafluorobutoxy;

$C_1$–$C_6$-haloalkoxy: $C_1$–$C_4$-haloalkoxy as mentioned above and, for example, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy or dodecafluorohexoxy;

$C_3$–$C_6$-cycloalkoxy: cyclopropoxy, cyclobutoxy, cyclopentoxy or cyclohexoxy;

$C_1$–$C_4$-alkylthio: methylthio, ethylthio, propylthio, 1-methylethylthio, butylthio, 1-methylpropylthio, 2-methylpropylthio or 1,1-dimethylethylthio;

$C_1$–$C_6$-alkylthio: $C_1$–$C_4$-alkylthio as mentioned above and, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio;

$C_3$–$C_6$-alkenyl: prop-1-en-1-yl, prop-2-en-1-yl, 1-methylethenyl, buten-1-yl, buten-2-yl, buten-3-yl, 1-methylprop-1-en-1-yl, 2-methylprop-1-en-1-yl, 1-methylprop-2-en-1-yl, 2-methylprop-2-en-1-yl, penten-1-yl, penten-2-yl, penten-3-yl, penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, hex-1-en-1-yl, hex-2-en-1-yl, hex-3-en-1-yl, hex-4-en-1-yl, hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl or 1-ethyl-2-methylprop-2-en-1-yl;

$C_2$–$C_6$-alkenyl: $C_3$–$C_6$-alkenyl as mentioned above, and also ethenyl;

$C_3$–$C_6$-alkynyl: prop-1-yn-1-yl, prop-2-yn-1-yl, but-1-yn-1-yl, but-1-yn-3-yl, but-1-yn-4-yl but-2-yn-1-yl, pent-1-yn-1-yl, pent-1-yn-3-yl, pent-1-yn-4-yl, pent-1-yn-5-yl, pent-2-yn-1-yl, pent-2-yn-4-yl, pent-2-yn-5-yl, 3-methylbut-1-yn-3-yl, 3-methylbut-1-yn-4-yl, hex-1-yn-1-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-yl, hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl;

$C_2$–$C_6$-alkynyl: $C_3$–$C_6$-alkynyl as mentioned above, and also ethynyl:

$C_3$–$C_4$-cycloalkyl: cyclopropyl or cyclobutyl;

$C_3$–$C_6$-cycloalkyl: $C_3$–$C_4$-cycloalkyl as mentioned above, and also cyclopentyl or cyclohexyl;

$C_3$–$C_6$-alkenyloxy: for example prop-1-en-1-yloxy, prop-2-en-1-yloxy, 1-methylethenyloxy, buten-1-yloxy, buten-2-yloxy, buten-3-yloxy, 1-methylprop-1-en-1-yloxy, 2-methylprop-1-en-1-yloxy, 1-methylprop-2-en-1-yloxy, 2-methylprop-2-en-1-yloxy, penten-1-yloxy, penten-2-yloxy, penten-3-yloxy, penten-4-yloxy, 1-methylbut-1-en-1-yloxy, 2-methylbut-1-en-1-yloxy, 3-methylbut-1-en-1-yloxy, 1-methylbut-2-en-1-yloxy, 2-methylbut-2-en-1-yloxy, 3-methylbut-2-en-1-yloxy, 1-methylbut-3-en-1-yloxy, 2-methylbut-3-en-1-yloxy, 3-methylbut-3-en-1-yloxy, 1,1-dimethylprop-2-en-1-yloxy, 1,2-dimethylprop-1-en-1-yloxy, 1,2-dimethylprop-2-en-1-yloxy, 1-ethylprop-1-en-2-yloxy, 1-ethylprop-2-en-1-yloxy, hex-1-en-1-yloxy, hex-2-en-1-yloxy, hex-3-en-1-yloxy, hex-4-en-1-yloxy, hex-5-en-1-yloxy, 1-methylpent-1-en-1-yloxy, 2-methylpent-1-en-1-yloxy, 3-methylpent-1-en-1-yloxy, 4-methylpent-1-en-1-yloxy, 1-methylpent-2-en-1-yloxy, 2-methylpent-2-en-1-yloxy, 3-methylpent-2-en-1-yloxy, 4-methylpent-2-en-1-yloxy, 1-methylpent-3-en-1-yloxy, 2-methylpent-3-en-1-yloxy, 3-methylpent-3-en-1-yloxy, 4-methylpent-3-en-1-yloxy, 1-methylpent-4-en-1-yloxy, 2-methylpent-4-en-1-yloxy, 3-methylpent-4-en-1-yloxy, 4-methylpent-4-en-1-yloxy, 1,1-dimethylbut-2-en-1-yloxy, 1,1-dimethylbut-3-en-1-yloxy, 1,2-dimethylbut-1-en-1-yloxy, 1,2-dimethylbut-2-en-1-yloxy, 1,2-dimethylbut-3-en-1-yloxy, 1,3-dimethylbut-1-en-1-yloxy, 1,3-dimethylbut-2-en-1-yloxy, 1,3-dimethylbut-3-en-1-yloxy, 2,2-dimethylbut-3-en-1-yloxy, 2,3-dimethylbut-1-en-1-yloxy, 2,3-dimethylbut-2-en-1-yloxy, 2,3-dimethylbut-3-en-1-yloxy, 3,3-dimethylbut-1-en-1-yloxy, 3,3-dimethylbut-2-en-1-yloxy, 1-ethylbut-1-en-1-yloxy, 1-ethylbut-2-en-1-yloxy, 1-ethylbut-3-en-1-yloxy, 2-ethylbut-1-en-1-yloxy, 2-ethylbut-2-en-1-yloxy, 2-ethylbut-3-en-1-yloxy, 1,1,2-trimethylprop-2-en-1-yloxy, 1-ethyl-1-methylprop-2-en-1-yloxy, 1-ethyl-1-methylprop-2-en-1-yloxy or 1-ethyl-2-methylprop-2-en-1-yloxy;

$C_3$–$C_6$-alkynyloxy: for example prop-1-yn-1-yloxy, prop-2-yn-1-yloxy, but-1-yn-1-yloxy, but-1-yn-3-yloxy, but-1-yn-4-yloxy, but-2-yn-1-yloxy, pent-1-yn-1-yloxy, pent-1-yn-3-yloxy, pent-1-yn-4-yloxy, pent-1-yn-5-yloxy, pent-2-yn-1-yloxy, pent-2-yn-4-yloxy, pent-2-yn-5-yloxy, 3-methylbut-1-yn-3-yloxy, 3-methylbut-1-yn-4-yloxy, hex-1-yn-1-yloxy, hex-1-yn-3-yloxy, hex-1-yn-4-yloxy, hex-1-yn-5-yloxy, hex-1-yn-6-yloxy, hex-2-yn-1-yloxy, hex-2-yn-4-yloxy, hex-2-yn-5-yloxy, hex-2-yn-6-yloxy, hex-3-yn-1-yloxy, hex-3-yn-2-yloxy, 3-methylpent-1-yn-1-yloxy, 3-methylpent-1-yn-3-yloxy, 3-methylpent-1-yn-4-yloxy, 3-methylpent-1-yn-5-yloxy, 4-methylpent-1-yn-1-yloxy, 4-methylpent-2-yn-4-yloxy or 4-methylpent-2-yn-5-yloxy;

$C_4$–$C_6$-cycloalkenyl: cyclobuten-1-yl, cyclobuten-3-yl, cyclopenten-1-yl, cyclopenten-3-yl, cyclohexen-1-yl, cyclohexen-3-yl or cyclohexen-4-yl;

heterocyclyl and the heterocyclyl radicals in heterocyclyloxy and heterocyclyl-$C_1$–$C_4$-alkyl: three- to seven-membered saturated or partially unsaturated mono- or polycyclic heterocycles which contain one to three hetero atoms selected from a group consisting of oxygen, nitrogen and sulfur, such as oxiranyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofuran-2-yl, 2,3-dihydrofuran-3-yl, 2,3-dihydrofuran-4-yl, 2,3-dihydrofuran-5-yl, 2,5-dihydrofuran-2-yl, 2,5-dihydrofuran-3-yl, 2,3-dihydrothien-2-yl, 2,3-dihydrothien-3-yl, 2,3-dihydrothien-4-yl, 2,3-dihydrothien-5-yl, 2,5-dihydrothien-2-yl, 2,5-dihydrothien-3-yl, 2,3-dihydropyrrol-2-yl, 2,3-dihydropyrrol-3-yl, 2,3-dihydropyrrol-4-yl, 2,3-dihydropyrrol-5-yl, 2,5-dihydropyrrol-2-yl, 2,5-dihydropyrrol-3-yl, 2,3-dihydroisoxazol-3-yl, 2,3-dihydroisoxazol-4-yl, 2,3-dihydroisoxazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisothiazol-3-yl, 2,3-dihydroisothiazol-4-yl, 2,3-dihydroisothiazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydropyrazol-3-yl, 2,3-dihydropyrazol-4-yl, 2,3-dihydropyrazol-5-yl, 4,5-dihydropyrazol-3-yl, 4,5-dihydropyrazol-4-yl, 4,5-dihydropyrazol-5-yl, 2,5-dihydropyrazol-3-yl, 2,5-dihydropyrazol-4-yl, 2,5-dihydropyrazol-5-yl, 2,3-dihydrooxazol-2-yl, 2,3-dihydrooxazol-4-yl, 2,3-dihydrooxazol-5-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrothiazol-2-yl, 2,3-dihydrothiazol-4-yl, 2,3-dihydrothiazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydroimidazol-2-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 2-morpholinyl, 3-morpholinyl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl, 1,2,4-tetrahydrotriazin-3-yl, 1,3-dihydrooxazin-2-yl, 2-tetrahydropyranyl, 3-tetrahydropyranyl, 4-tetrahydropyranyl, 2-tetrahydrothiopyranyl, 3-tetrahydrothiopyranyl, 4-tetrahydrothiopyranyl, 1,3-dioxolan-2-yl, 1,3-dioxolan-4-yl, 1,3-dithiolan-2-yl, 1,3-dithiolan-4-yl, 1,3-dioxan-2-yl, 1,3-dioxan-4-yl, 1,3-dioxan-5-yl, 1,3-dithian-2-yl, 1,3-dithian-4-yl, 1,3-dithian-5-yl, 3,4,5,6-tetrahydropyridin-2-yl, 4H-1,3-thiazin-2-yl, 4H-3,1-benzothiazin-2-yl, 1,1-dioxo-2,3,4,5-tetrahydrothien-2-yl, 2H-1,4-benzothiazin-3-yl, 2H-1,4-benzoxazin-3-yl or 1,3-dihydrooxazin-2-yl;

hetaryl and the hetaryl radicals in hetaryloxy and hetaryl-$C_1$–$C_4$-alkyl: aromatic mono- or polycyclic radicals which, in addition to carbon ring members, can additionally comprise one to four nitrogen atoms or one to three nitrogen atoms and one oxygen or one sulfur atom or one oxygen or one sulfur atom, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl or 1,2,4,5-tetrazin-3-yl, and the corresponding benzo-fused derivatives;

$C_2–C_6$-alkanediyl: for example ethane-1,2-diyl, propane-1,3-diyl, butane-1,4-diyl, pentane-1,5-diyl or hexane-1,6-diyl.

All phenyl and hetaryl rings are preferably unsubstituted or have attached to them one to three halogen atoms and/or one or two radicals from amongst the following group: nitro, cyano, methyl, trifluoromethyl, methoxy, trifluoromethoxy or methoxycarbonyl.

With a view to the use of the compounds of the formula I according to the invention as herbicides, the variables preferably have the following meanings, in each case alone or in combination:

$R^1$ is nitro, halogen, cyano, thiocyanato, $C_1–C_6$-alkyl, $C_1–C_6$-haloalkyl, $C_1–C_6$-alkoxy-$C_1–C_6$-alkyl, $C_2–C_6$-alkenyl, $C_2–C_6$-alkynyl, —$OR^6$ or —$S(O)_nR^8$; especially preferably nitro, halogen, eg. fluorine, chlorine or bromine, $C_1–C_6$-haloalkyl, —$OR^6$ or —$SO_2R^8$;

$R^2$ is hydrogen, nitro, halogen, cyano, thiocyanato, $C_1–C_6$-alkyl, $C_1–C_6$-haloalkyl, $C_1–C_6$-alkoxy-$C_1–C_6$-alkyl, $C_2–C_6$-alkenyl, $C_2–C_6$-alkynyl, —$OR^6$ or —$S(O)_nR^8$; especially preferably hydrogen, nitro, halogen, eg. fluorine, chlorine or bromine, $C_1–C_6$-alkyl, $C_1–C_6$-haloalkyl, —$OR^6$ or —$SO_2R^8$; particularly preferably nitro, halogen, eg. fluorine, chlorine or bromine, $C_1–C_6$-alkyl, eg. methyl or ethyl, $C_1–C_6$-haloalkyl, eg. difluoromethyl or trifluoromethyl, —$OR^6$ or —$SO_2R^8$;

$R^3$ is hydrogen, halogen, $C_1–C_6$-alkyl, $C_1–C_6$-haloalkyl, $C_1–C_6$-alkoxy, $C_2–C_6$-alkenyl or $C_2–C_6$-alkynyl; especially preferably hydrogen, halogen, eg. fluorine, chlorine or bromine, $C_1–C_4$-alkyl, eg. methyl or ethyl, $C_1–C_4$-haloalkyl, eg. trifluoromethyl, $C_1–C_4$-alkoxy, eg. methoxy or ethoxy, allyl or propargyl; particularly preferably hydrogen or methyl;

$R^4$ is hydrogen, nitro, halogen, cyano, thiocyanato, $C_1–C_6$-alkyl, $C_1–C_6$-haloalkyl, $C_3–C_6$-cycloalkyl, $C_2–C_6$-alkenyl, $C_4–C_6$-cycloalkenyl, $C_2–C_6$-alkynyl, $C_1–C_6$-alkoxy, $C_1–C_6$-alkylthio, $C_1–C_6$-haloalkoxy, —$COR^{10}$, —$CO_2R^{10}$, —$COSR^{10}$, —$CONR^{10}R^{11}$, —$C(R^{12})$=$NR^{13}$, —$PO(OR^{10})(OR^{11})$, $C_1–C_4$-alkyl which has attached to it a radical from amongst the following group: —$COR^{10}$, —$CO_2R^{10}$, —$COSR^{10}$, —$CONR^{10}R^{11}$ or —$C(R^{12})$=$NR^{13}$; heterocyclyl, heterocyclyl-$C_1–C_4$-alkyl, phenyl, phenyl-$C_1–C_4$-alkyl, hetaryl, hetaryl-$C_1–C_4$-alkyl, it being possible for the six last-mentioned radicals, in turn, to be substituted by one to three halogen atoms and/or one to three radicals from amongst the following group:
nitro, cyano, $C_1–C_4$-alkyl, $C_1–C_4$-haloalkyl, $C_1–C_4$-alkoxy, $C_1–C_4$-haloalkoxy, $C_1–C_4$-alkylcarbonyl, $C_1–C_4$-alkoxycarbonyl;

$R^5$ is hydrogen, nitro, halogen, cyano, thiocyanato, $C_1–C_6$-alkyl, $C_1–C_6$-haloalkyl, $C_3–C_6$-cycloalkyl, $C_2–C_6$-alkenyl, $C_4–C_6$-cycloalkenyl, $C_2–C_6$-alkynyl, $C_1–C_6$-alkoxy, $C_1–C_6$-alkylthio, $C_1–C_6$-haloalkoxy, —$COR^{10}$, —$CO_2R^{10}$, —$COSR^{10}$, —$CONR^{10}R^{11}$, —$C(R^{12})$=$NR^{13}$, —$PO(OR^{10})(OR^{11})$, $C_1–C_4$-alkyl which has attached to it a radical from amongst the following group: —$COR^{10}$, —$CO_2R^{10}$, —$COSR^{10}$, —$CONR^{10}R^{11}$ or —$C(R^{12})$=$NR^{13}$; heterocyclyl, heterocyclyl-$C_1–C_4$-alkyl, phenyl, phenyl-$C_1–C_4$-alkyl, hetaryl, hetaryl-$C_1–C_4$-alkyl, it being possible for the six last-mentioned radicals, in turn, to be substituted by one to three halogen atoms and/or one to three radicals from amongst the following group: nitro, cyano, $C_1–C_4$-alkyl, $C_1–C_4$-haloalkyl, $C_1–C_4$-alkoxy, $C_1–C_4$-haloalkoxy, $C_1–C_4$-alkylcarbonyl, $C_1–C_4$-alkoxycarbonyl;
especially preferably hydrogen, halogen, cyano, thiocyanato, $C_1–C_6$-alkyl, $C_1–C_6$-haloalkyl, —$COR^{10}$, —$CO_2R^{10}$, —$COSR^{10}$, —$CONR^{10}R^{11}$ or —$PO(OR^{10})(OR^{11})$; or $R^4$ and $R^5$ together form a $C_2–C_6$-alkanediyl chain which can be mono- to tetrasubstituted by $C_1–C_4$-alkyl and/or can be interrupted by oxygen or sulfur or by a nitrogen which is unsubstituted or substituted by $C_1–C_4$-alkyl, for example butane-1,4-diyl, pentane-1,5-diyl, hexane-1,6-diyl, 3-oxapentane-1,5-diyl or 3-methyl-3-azapentane-1,5-diyl;

n is 0 or 2

$R^6$ is hydrogen, $C_1–C_6$-alkyl, $C_1–C_6$-haloalkyl, $C_1–C_6$-alkoxy-$C_2–C_6$-alkyl, $C_3–C_6$-alkenyl or $C_3–C_6$-alkynyl; especially preferably $C_1–C_4$-alkyl, eg. methyl or ethyl, $C_1–C_4$-haloalkyl, eg. trifluoromethyl or difluoromethyl, $C_1–C_4$-alkoxy-$C_1–C_4$-alkyl, eg. methoxyethyl, allyl or propargyl;

$R^8$ is $C_1–C_6$-alkyl, $C_1–C_6$-haloalkyl, $C_1–C_6$-alkoxy-$C_2–C_6$-alkyl, $C_3–C_6$-alkenyl or $C_3–C_6$-alkynyl; especially preferably $C_1–C_4$-alkyl, eg. methyl or ethyl, $C_1–C_4$-haloalkyl, eg. trifluoromethyl, difluoromethyl, $C_1–C_4$-alkoxy-$C_1–C_4$-alkyl, eg. methoxyethyl, allyl or propargyl;

$R^{10}$ is hydrogen, $C_1–C_6$-alkyl, $C_3–C_6$-cycloalkyl, $C_1–C_6$-haloalkyl, $C_3–C_6$-alkenyl, $C_3–C_6$-alkynyl, phenyl or benzyl; especially preferably hydrogen, $C_1–C_4$-alkyl, eg. methyl or ethyl, $C_1–C_4$-haloalkyl, eg. trifluoromethyl, allyl, propargyl and benzyl;

$R^{11}$ is hydrogen, $C_1–C_6$-alkyl, $C_3–C_6$-alkenyl or $C_3–C_6$-alkynyl; or $R^{10}$ and $R^{11}$ together form a $C_2–C_6$-alkanediyl chain which can be mono- to tetrasubstituted by $C_1–C_4$-alkyl;

$R^{12}$ is hydrogen, $C_1–C_6$-alkyl, $C_1–C_6$-haloalkyl, $C_1–C_6$-alkoxy, $C_1–C_6$-alkoxycarbonyl, $C_3–C_6$-cycloalkyl, $C_2–C_6$-alkenyl, $C_2–C_6$-alkynyl, phenyl or benzyl; especially preferably hydrogen, $C_1–C_4$-alkyl, eg. methyl or ethyl, $C_1–C_4$-alkoxycarbonyl, eg. methoxycarbonyl or ethoxycarbonyl, $C_1–C_4$-haloalkyl, eg. trifluoromethyl, or $C_1–C_4$-alkoxy, eg. methoxy or ethoxy;

$R^{13}$ is $C_1–C_6$-alkyl, $C_1–C_6$-haloalkyl, $C_3–C_6$-cycloalkyl, $C_3–C_6$-alkenyl, $C_3–C_6$-alkynyl, $C_1–C_6$-alkoxy, $C_1–C_6$-haloalkoxy, $C_3–C_6$-cycloalkyloxy, $C_3–C_6$-alkenyloxy, $C_3–C_6$-alkynyloxy, phenyl, benzyl, or benzyloxy; especially preferably $C_1–C_4$-alkyl, eg. methyl or ethyl, $C_1–C_4$-alkoxy, eg. methoxy or ethoxy, allyloxy, propargyloxy, benzyl or benzyloxy;

$R^{14}$, $R^{15}$, $R^{17}$, $R^{19}$ are hydrogen or $C_1–C_4$-alkyl; especially preferably hydrogen, methyl or ethyl;

$R^{16}$ is hydrogen, $C_1–C_4$-alkyl, $C_1–C_4$-haloalkyl, $C_3–C_4$-cycloalkyl, it optionally being possible for the three last-mentioned groups to have attached to them one to three of the following substituents: $C_1–C_4$-alkoxy or $C_1–C_4$-alkylthio; tetrahydropyran-2-yl, tetrahydropyran-3-yl, tetrahydropyran-4-yl, tetrahydrothiopyran-2-yl, tetrahydrothiopyran-3-yl, tetrahydrothiopyran-4-yl, 1,3-dioxolan-2-yl, 1,3-dioxan-2-yl, 1,3-oxathiolan-2-yl, 1,3-oxathian-2-yl, 1,3-dithian-2-yl or 1,3-dithiolan-2-yl, it being possible for each of the six last-mentioned groups to have attached to them one to three $C_1–C_4$-alkyl radicals; especially preferably hydrogen, methyl, ethyl, cyclopropyl, di(methoxy)methyl, di(ethoxy)methyl, 2-ethylthiopropyl, tetrahydropyran-2-yl, tetrahydropyran-3-yl, tetrahydropyran-4-yl, tetrahydrothiopyran-2-yl, tetrahydrothiopyran-3-yl, tetrahydrothiopyran-4-yl, 1,3-dioxolan-2-yl, 1,3-dioxan-2-yl, 5,5-dimethyl-1,3-dioxan-2-yl, 1,3-oxathiolan-2-yl, 1,3-oxathian-2-yl, 1,3-dithiolan-2-yl, 5,5-dimethyl-1,3-dithian-2-yl or 1-methylthiocyclopropyl;

$R^{18}$ is hydrogen, $C_1$–$C_4$-alkyl or $C_1$–$C_4$-alkoxycarbonyl; especially preferably hydrogen, methyl or methoxycarbonyl; particularly preferably hydrogen or methyl.

Equally, it may advantageously be suitable for $R^{16}$ and $R^{19}$ to form a π bond, so that a double-bond system results.

The $CR^{16}R^{17}$ unit may advantageously also be replaced by C=O.

Extraordinarily preferred compounds of the formula I are those where $R^1$ is nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^6$ or —$S(O)_nR^8$;

$R^2$ is hydrogen or a radical mentioned under $R^1$, as above.

Especially extraordinarily preferred are compounds of the formula I where $R^1$ is nitro, halogen, eg. fluorine, chlorine or bromine, $C_1$–$C_6$-haloalkyl, $OR^6$ or $SO_2R^8$;

$R^2$ is nitro, halogen, eg. fluorine, chlorine or bromine, $C_1$–$C_6$-alkyl, eg. methyl or ethyl, $C_1$–$C_6$-haloalkyl, $OR^6$ or $SO_2R^8$, eg. methylsulfonyl or ethylsulfonyl.

Equally extraordinarily preferred compounds of the formula I are those where $R^4$ [lacuna] hydrogen, nitro, halogen, cyano, thiocyanato, $C_1$–$C_6$-alkyl, $C_1$–$C_6$-haloalkyl, $C_1$–$C_6$-cycloalkyl, $C_2$–$C_6$-alkenyl, $C_4$–$C_6$-cycloalkenyl, $C_2$–$C_6$-alkynyl, $C_1$–$C_6$-alkoxy, $C_1$–$C_6$-alkylthio, $C_1$–$C_6$-haloalkoxy, —$COR^{10}$, —$CO_2R^{10}$, —$COSR^{10}$, —$CONR^{10}R^{11}$, —$C(R^{12})$=$NR^{13}$, —$PO(OR^{10})(OR^{11})$, $C_1$–$C_4$-alkyl which has attached to it a radical from amongst the following group: —$COR^{10}$, —$CO_2R^{10}$, —$COSR^{10}$, —$CONR^{10}R^{11}$ or —$C(R'^2)$=$NR^{13}$; heterocyclyl, heterocyclyl-$C_1$–$C_4$-alkyl, phenyl, phenyl-$C_1$–$C_4$-alkyl, hetaryl, hetaryl-$C_1$–$C_4$-alkyl, it being possible for the six last-mentioned radicals to be substituted;

$R^5$ [lacuna] hydrogen, halogen, cyano, thiocyanato, $C_1$–$C_6$-alkyl, $C_1$–$C_6$-haloalkyl, —$COR^{10}$, —$CO_2R^{10}$, —$COSR^{10}$, —$CONR^{10}R^{11}$ or —$PO(OR^{10})(OR^{11})$; or $R^4$ and $R^5$ together form a $C_2$–$C_6$-alkanediyl chain which can be mono- to tetrasubstituted by $C_1$–$C_4$-alkyl and/or can be interrupted by oxygen or sulfur or a nitrogen which is unsubstituted or substituted by $C_1$–$C_4$-alkyl.

Equally extraordinarily preferred are those compounds of the formula I where $R^{16}$ is hydrogen, $C_1$–$C_4$-alkyl, $C_1$–$C_4$-haloalkyl, $C_3$–$C_4$-cycloalkyl, it being possible for the three last-mentioned substituents to have attached to them two or three of the following substituents: $C_1$–$C_4$-alkylthio or $C_1$–$C_4$-alkoxy.

Equally extraordinarily preferred compounds of the formula I are those where $R^4$ is nitro, halogen, cyano, thiocyanato, $C_1$–$C_6$-haloalkyl, $C_3$–$C_6$-cycloalkyl, $C_2$–$C_6$-alkenyl, $C_4$–$C_6$-cycloalkenyl, $C_2$–$C_6$-alkynyl, $C_1$–$C_6$-alkoxy, $C_1$–$C_6$-alkylthio, $C_1$–$C_6$-haloalkoxy, —$COR^{10}$, —$CO_2R_{10}$, —$COSR^{10}$, —$CONR^{10}R^{11}$, —$C(R^{12})$=$NR^{13}$, —$PO(OR^{10})(OR^{11})$, $C_1$–$C_4$-alkyl which has attached to it a radical from amongst the following group: —$COR^{10}$, —$CO_2R^{10}$, —$COSR^{10}$, —$CONR^{10}R^{11}$ or —$C(R^{12})$=$NR^{13}$; heterocyclyl, heterocyclyl-$C_1$–$C_4$-alkyl, phenyl, phenyl-$C_1$–$C_4$-alkyl, hetaryl, hetaryl-$C_1$–$C_4$-alkyl, it being possible for the six last-mentioned radicals to be substituted;

$R^5$ is hydrogen, halogen, cyano, $C_1$–$C_6$-alkyl, $C_1$–$C_6$-haloalkyl, —$COR^{10}$, —$CO_2R^{10}$, —$COSR^{10}$, —$CONR^{10}R^{11}$ or —$PO(OR^{10})(OR^{11})$; or $R^4$ and $R^5$ together form a $C_2$–$C_6$-alkanediyl chain which can be mono- to tetrasubstituted by $C_1$–$C_4$-alkyl and/or can be interrupted by oxygen or sulfur or a nitrogen which is unsubstituted or substituted by $C_1$–$C_4$-alkyl;

Equally especially preferred compounds of the formula I are those where $R^1$ is nitro, halogen, $C_1$–$C_6$-haloalkyl or $C_1$–$C_6$-alkylsulfonyl; in particular nitro, chlorine, trifluoromethyl, methylsulfonyl or ethylsulfonyl;

$R^2$ is nitro, halogen, $C_1$–$C_6$-alkyl, $C_1$–$C_6$-haloalkyl, $C_1$–$C_6$-alkoxy or $C_1$–$C_6$-alkylsulfonyl; in particular nitro, chlorine, methyl, trifluoromethyl, methoxy or methylsulfonyl;

$R^3$ is hydrogen or $C_1$–$C_6$-alkyl; in particular hydrogen or methyl; preferably hydrogen;

$R^4$ is hydrogen, halogen, cyano, $C_1$–$C_4$-alkyl, $C_1$–$C_4$-hydroxyalkyl, $C_1$–$C_4$-alkoxy, $C_1$–$C_4$-alkylcarbonyl, $C_1$–$C_4$-alkoxycarbonyl or —$C(R^{12})$=$NR^{13}$; in particular hydrogen, chlorine, bromine, cyano, methyl, ethyl, 2-hydroxyethyl, methoxy, ethoxy, methylcarbonyl, ethylcarbonyl, methoxycarbonyl, ethoxycarbonyl or —$C(R^{12})$-=$NR^{13}$;

$R^5$ is hydrogen, halogen, $C_1$–$C_4$-alkyl or $C_1$–$C_4$-alkoxy; in particuclar hydrogen, halogen, methyl, ethyl, methoxy or ethoxy;

$R^{12}$ is hydrogen, $C_1$–$C_4$-alkyl or $C_1$–$C_4$-alkoxy; in particular hydrogen or methyl;

$R^{13}$ is $C_1$–$C_6$-alkyl or $C_1$–$C_6$-alkoxy; in particular methoxy or ethoxy;

$R^{14}$, $R^{15}$, $R^{16}$, $R^{17}$, $R^{18}$ and $R^{19}$ are hydrogen or $C_1$–$C_4$-alkyl; in particular hydrogen or methyl;

or the $CR^{16}R^{17}$ unit can be replaced by C=O; and where the definitions of radicals $R^1$ to $R^{19}$ have a particular meaning for the compounds of the formula I according to the invention, not only in combination with each other, but also in each case taken alone.

Especially extraordinarily preferred are compounds of the formula Ia (= I where $R^1$ is bonded in the 4-position of the phenyl ring and $R^2$ is bonded in the 2-position of the phenyl ring).

Ia

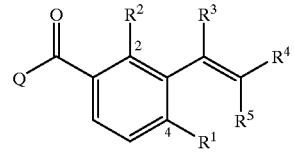

Particularly extraordinarily preferred are the compounds Ia1 (= I where $R^1$=Cl, $R^{14}$, $R^{15}$, $R^{16}$, $R^{17}$, $R^{18}$, $R^{19}$=H, $R^1$ being bonded in the 4-position of the phenyl ring and $R^2$ being bonded in the 2-position of the phenyl ring), in particular the compounds of Table 1, the definitions of the radicals $R^2$ to $R^5$ not only having a special meaning for the compounds according to the invention in combination with each other, but also in each case on their own.

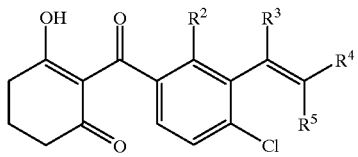

Ia1

TABLE 1

| No. | R² | R³ | R⁴ | R⁵ |
|---|---|---|---|---|
| Ia1.001 | Cl | H | H | H |
| Ia1.002 | Cl | H | CH₃ | H |
| Ia1.003 | Cl | H | CH₃ | CH₃ |
| Ia1.004 | Cl | H | C₂H₅ | H |
| Ia1.005 | Cl | H | n—C₃H₇ | H |
| Ia1.006 | Cl | H | n—C₄H₉ | H |
| Ia1.007 | Cl | H | CH(CH₃)₂ | H |
| Ia1.008 | Cl | H | cyclo—C₃H₅ | H |
| Ia1.009 | Cl | H | cyclo—C₄H₇ | H |
| Ia1.010 | Cl | H | cyclo—C₅H₉ | H |
| Ia1.011 | Cl | H | cyclo—C₆H₁₁ | H |
| Ia1.012 | Cl | H | C₆H₅ | H |
| Ia1.013 | Cl | H | CH₂—C₆H₅ | H |
| Ia1.014 | Cl | H | 2-furyl | H |
| Ia1.015 | Cl | H | 3-furyl | H |
| Ia1.016 | Cl | H | 2-thienyl | H |
| Ia1.017 | Cl | H | 3-thienyl | H |
| Ia1.018 | Cl | H | 1,3-dioxan-2-yl | H |
| Ia1.019 | Cl | H | CHO | H |
| Ia1.020 | Cl | H | COCH₃ | H |
| Ia1.021 | Cl | H | COOCH₃ | H |
| Ia1.022 | Cl | H | COOC₂H₅ | H |
| Ia1.023 | Cl | H | OCH₃ | H |
| Ia1.024 | Cl | H | CN | H |
| Ia1.025 | Cl | H | SCH₃ | H |
| Ia1.026 | Cl | H | COCF₃ | H |
| Ia1.027 | Cl | H | COC₆H₅ | H |
| Ia1.028 | Cl | H | CH=NOCH₃ | H |
| Ia1.029 | Cl | H | CH=NOC₂H₅ | H |
| Ia1.030 | Cl | H | C(CH₃)=NOCH₃ | H |
| Ia1.031 | CH₃ | H | H | H |
| Ia1.032 | CH₃ | H | CH₃ | H |
| Ia1.033 | CH₃ | H | CH₃ | CH₃ |
| Ia1.034 | CH₃ | H | C₂H₅ | H |
| Ia1.035 | CH₃ | H | n—C₃H₇ | H |
| Ia1.036 | CH₃ | H | n—C₄H₉ | H |
| Ia1.037 | CH₃ | H | CHO | H |
| Ia1.038 | CH₃ | H | COCH₃ | H |
| Ia1.039 | CH₃ | H | COOCH₃ | H |
| Ia1.040 | CH₃ | H | OCH₃ | H |
| Ia1.041 | CH₃ | H | C₆H₅ | H |
| Ia1.042 | CH₃ | H | C₆H₅ | CH₃ |
| Ia1.043 | CH₃ | H | C₆H₅ | C₂H₅ |
| Ia1.044 | CH₃ | H | CH₂—CHO | H |
| Ia1.045 | CH₃ | H | COOCH₂C₆H₅ | w |
| Ia1.046 | CH₃ | Cl | CH₃ | H |
| Ia1.047 | CH₃ | CH₃ | CH₃ | H |
| Ia1.048 | CH₃ | C₂H₅ | CH₃ | H |
| Ia1.049 | CH₃ | CF₃ | CH₃ | H |
| Ia1.050 | CH₃ | OCH₃ | CH₃ | H |
| Ia1.051 | CH₃ | OC₂H₅ | CH₃ | H |
| Ia1.052 | CH₃ | CH₂—C≡CH | CH₃ | H |
| Ia1.053 | CH₃ | CH₂—CH=CH₂ | CH₃ | H |
| Ia1.054 | CH₃ | Cl | C₂H₅ | H |
| Ia1.055 | CH₃ | CH₃ | C₂H₅ | H |
| Ia1.056 | CH₃ | CF₃ | C₂H₅ | H |
| Ia1.057 | CH₃ | OCH₃ | C₂H₅ | H |
| Ia1.058 | CH₃ | OC₂H₅ | C₂H₅ | H |
| Ia1.059 | CH₃ | CH₂—C≡CH | C₂H₅ | H |
| Ia1.060 | CH₃ | CH₂—CH=CH | C₂H₅ | H |
| Ia1.061 | OCH₃ | H | H | H |
| Ia1.062 | OCH₃ | H | CH₃ | H |
| Ia1.063 | OCH₃ | H | C₂H₅ | H |
| Ia1.064 | OCH₃ | H | n—C₃H₇ | H |
| Ia1.065 | OCH₃ | H | n—C₄H₉ | H |

TABLE 1-continued

| No. | R² | R³ | R⁴ | R⁵ |
|---|---|---|---|---|
| Ia1.066 | OCH₃ | H | CHO | H |
| Ia1.067 | OCH₃ | H | COCH₃ | H |
| Ia1.068 | OCH₃ | H | COOCH₃ | H |
| Ia1.069 | OCH₃ | H | OCH₃ | H |
| Ia1.070 | OCH₃ | H | C₆H₅ | H |
| Ia1.071 | OCH₃ | H | CH=NOCH₃ | H |
| Ia1.072 | OCH₃ | H | C(CH₃)=NOCH₃ | H |
| Ia1.073 | OCH₃ | CH₃ | 2—Cl—C₆H₄ | H |
| Ia1.074 | OCH₃ | CH₃ | 3—Br—C₆H₄ | H |
| Ia1.075 | OCH₃ | CH₃ | 4—F—C₆H₄ | H |
| Ia1.076 | OCH₃ | CH₃ | 2,4—Cl₂—C₆H₃ | H |
| Ia1.077 | OCH₃ | CH₃ | 2—NO₂—C₆H₄ | H |
| Ia1.078 | OCH₃ | CH₃ | 3—CN—C₆H₄ | H |
| Ia1.079 | OCH₃ | CH₃ | 4—CH₃—C₆H₄ | H |
| Ia1.080 | OCH₃ | CH₃ | 2—OCH₃—C₆H₄ | H |
| Ia1.081 | OCH₃ | CH₃ | 3—CF₃—C₆H₄ | H |
| Ia1.082 | OCH₃ | CH₃ | 4—OCF₃—C₆H₄ | H |
| Ia1.083 | OCH₃ | CH₃ | 2—CH₃—C₆H₄ | H |
| Ia1.084 | OCH₃ | CH₃ | 3—CH₃—C₆H₄ | H |
| Ia1.085 | OCH₃ | CH₃ | 2—COCH₃—C₆H₄ | H |
| Ia1.086 | OCH₃ | CH₃ | 3—COOCH₃—C₆H₄ | H |
| Ia1.O87 | OCH₃ | CH₃ | 4—CF₃—C₆H₄ | H |
| Ia1.088 | OCH₃ | CH₃ | 2—CF₃—C₆H₄ | H |
| Ia1.089 | OCH₃ | CH₃ | 3—OCH₃—C₆H₄ | H |
| Ia1.090 | OCH₃ | CH₃ | 4—OCH₃—C₆H₄ | H |
| Ia1.091 | CF₃ | H | H | H |
| Ia1.092 | CF₃ | H | CH₃ | H |
| Ia1.093 | CF₃ | H | C₂H₅ | H |
| Ia1.094 | CF₃ | H | n—C₃H₇ | H |
| Ia1.095 | CF₃ | H | n-C₄H₉ | H |
| Ia1.096 | CF₃ | H | CHO | H |
| Ia1.097 | CF₃ | H | COCH₃ | H |
| Ia1.098 | CF₃ | H | COOCH₃ | H |
| Ia1.099 | CF₃ | H | OCH₃ | H |
| Ia1.100 | CF₃ | H | C₆H₅ | H |
| Ia1.101 | CF₃ | H | CH=NOCH₃ | H |
| Ia1.102 | CF₃ | H | C(CH₃)=NOCH₃ | H |
| Ia1.103 | CF₃ | H | 2-furyl | CH₃ |
| Ia1.104 | CF₃ | H | 3-furyl | CH₃ |
| Ia1.105 | CF₃ | H | 2-thienyl | CH₃ |
| Ia1.106 | CF₃ | H | 3-thienyl | CH₃ |
| Ia1.107 | CF₃ | H | 2-pyridyl | CH₃ |
| Ia1.108 | CF₃ | H | 3-pyridyl | CH₃ |
| Ia1.109 | CF₃ | H | 4-pyridyl | CH₃ |
| Ia1.110 | CF₃ | H | 2-thiazolyl | CH₃ |
| Ia1.111 | CF₃ | H | 4-thiazolyl | CH₃ |
| Ia1.112 | CF₃ | H | 5-thiazolyl | CH₃ |
| Ia1.113 | CF₃ | H | 2-pyrrolyl | CH₃ |
| Ia1.114 | CF₃ | H | 3-pyrrolyl | CH₃ |
| Ia1.115 | CF₃ | H | 4-pyrrolyl | CH₃ |
| Ia1.116 | CF₃ | H | 3 isoxazolyl | CH₃ |
| Ia1.117 | CF₃ | H | 4-isoxazolyl | CH₃ |
| Ia1.118 | CF₃ | H | 5-isoxazolyl | CH₃ |
| Ia1.119 | CF₃ | H | 2-oxazolyl | CH₃ |
| Ia1.120 | CF₃ | H | 4-oxazolyl | CH₃ |
| Ia1.121 | SO₂CH₃ | H | H | H |
| Ia1.122 | SO₂CH₃ | H | CH₃ | H |
| Ia1.123 | SO₂CH₃ | H | C₂H₅ | H |
| Ia1.124 | SO₂CH₃ | H | n—C₃H₇ | H |
| Ia1.125 | SO₂CH₃ | H | n—C₄H₉ | H |
| Ia1.126 | SO₂CH₃ | H | CHO | H |
| Ia1.127 | SO₂CH₃ | H | COCH₃ | H |
| Ia1.128 | SO₂CH₃ | H | COOCH₃ | H |
| Ia1.129 | SO₂CH₃ | H | OCH₃ | H |
| Ia1.130 | SO₂CH₃ | H | C₆H₅ | H |
| Ia1.131 | SO₂CH₃ | H | CH=NOCH₃ | H |
| Ia1.132 | SO₂CH₃ | H | C(CH₃)=NOCH₃ | H |
| Ia1.133 | SO₂CH₃ | C₂H₅ | 5-oxazolyl | H |
| Ia1.134 | SO₂CH₃ | C₂H₅ | 3-pyrazolyl | H |
| Ia1.135 | SO₂CH₃ | C₂H₅ | 4-pyrazolyl | H |
| Ia1.136 | SO₂CH₃ | C₂H₅ | 5-pyrazolyl | H |
| Ia1.137 | SO₂CH₃ | C₂H₅ | 2-imidazolyl | H |
| Ia1.138 | SO₂CH₃ | C₂H₅ | 4-imidazolyl | H |
| Ia1.139 | SO₂CH₃ | C₂H₅ | 5-imidazolyl | H |
| Ia1.140 | SO₂CH₃ | C₂H₅ | 2-pyrimidinyl | H |
| Ia1.141 | SO₂CH₃ | C₂H₅ | 4-pyrimidinyl | H |
| Ia1.142 | SO₂CH₃ | C₂H₅ | 5-pyrimidinyl | H |

TABLE 1-continued

| No. | $R^2$ | $R^3$ | $R^4$ | $R^5$ |
|---|---|---|---|---|
| Ia1.143 | $SO_2CH_3$ | $C_2H_5$ | 1,3-dioxolan-2-yl | H |
| Ia1.144 | $SO_2CH_3$ | $C_2H_5$ | 1,3-dioxolan-4-yl | H |
| Ia1.145 | $SO_2CH_3$ | $C_2H_5$ | 1,3-dioxan-2-yl | H |
| Ia1.146 | $SO_2CH_3$ | $C_2H_5$ | 3-pyridazinyl | H |
| Ia1.147 | $SO_2CH_3$ | $C_2H_5$ | 4-pyridazinyl | H |
| Ia1.148 | $SO_2CH_3$ | $C_2H_5$ | 2-pyrazinyl | H |
| Ia1.149 | $SO_2CH_3$ | $C_2H_5$ | 2-pyridyl | H |
| Ia1.150 | $SO_2CH_3$ | $C_2H_5$ | 2-N-methylpyrrolyl | H |
| Ia1.151 | $NO_2$ | H | H | H |
| Ia1.152 | $NO_2$ | H | $CH_3$ | H |
| Ia1.153 | $NO_2$ | H | $C_2H_5$ | H |
| Ia1.154 | $NO_2$ | H | $n-C_3H_7$ | H |
| Ia1.155 | $NO_2$ | H | $n-C_4H_9$ | H |
| Ia1.156 | $NO_2$ | H | CHO | H |
| Ia1.157 | $NO_2$ | H | $COCH_3$ | H |
| Ia1.158 | $NO_2$ | H | $COOCH_3$ | H |
| Ia1.159 | $NO_2$ | H | $OCH_3$ | H |
| Ia1.160 | $NO_2$ | H | $C_6H_5$ | H |
| Ia1.161 | $NO_2$ | H | $CH=NOCH_3$ | H |
| Ia1.162 | $NO_2$ | H | $C(CH_3)=NOCH_3$ | H |
| Ia1.163 | $NO_2$ | H | COOH | $C_2H_5$ |
| Ia1.164 | $NO_2$ | H | COOMe | $C_2H_5$ |
| Ia1.165 | $NO_2$ | H | $COOC_2H_5$ | $C_2H_5$ |
| Ia1.166 | $NO_2$ | H | $COOCH_2C_6H_5$ | $C_2H_5$ |
| Ia1.167 | $NO_2$ | H | $COOC(CH_3)_3$ | $C_2H_5$ |
| Ia1.168 | $NO_2$ | H | $CH=NOCH_3$ | $C_2H_5$ |
| Ia1.169 | $NO_2$ | H | $CH=NOC_2H_5$ | $C_2H_5$ |
| Ia1.170 | $NO_2$ | H | $CH=NOCH_2C_6H_5$ | $C_2H_5$ |
| Ia1.171 | $NO_2$ | H | $CH=NOCH(CH_3)_2$ | $C_2H_5$ |
| Ia1.172 | $NO_2$ | H | $C(CH_3)=NOCH_3$ | $C_2H_5$ |
| Ia1.173 | $NO_2$ | H | $C(CH_3)=NOC_2H_5$ | $C_2H_5$ |
| Ia1.174 | $NO_2$ | H | $C(CH_3)=NOCH(CH_3)_2$ | $C_2H_5$ |
| Ia1.175 | $NO_2$ | H | $C(CH_3)=NOCH_2C_6H_5$ | $C_2H_5$ |
| Ia1.176 | $NO_2$ | H | $CH=NOCH_2-CH=CH_2$ | $C_2H_5$ |
| Ia1.177 | $NO_2$ | H | $CH=NOCH_2-C\equiv CH$ | $C_2H_5$ |
| Ia1.178 | $NO_2$ | H | $CH_2-CHO$ | $C_2H_5$ |
| Ia1.179 | $NO_2$ | H | $CH_2-CH=NOCH_3$ | $C_2H_5$ |
| Ia1.180 | $NO_2$ | H | $CH_2-CH=NOC_2H_5$ | $C_2H_5$ |

Equally particularly extraordinarily preferred are the compounds Ia2, in particular the compounds Ia2.001–Ia2.180, which differ from the corresponding compounds Ia1.001–Ia1.180 by the fact that $R^{16}$ is methyl:

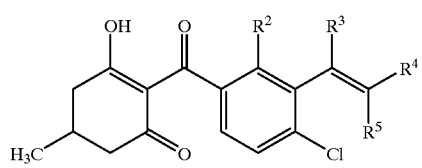

Ia2

Equally particularly extraordinarily preferred are the compounds Ia3, in particular the compounds Ia3.001–Ia3.180, which differ from the corresponding compounds Ia1.001–Ia1.180 by the fact that $R^{16}$ and $R^{17}$ are in each case methyl:

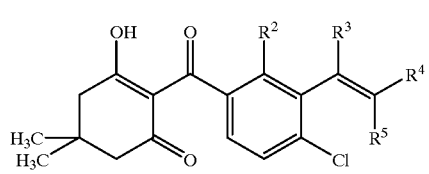

Ia3

Equally particularly extraordinarily preferred are the compounds Ia4, in particular the compounds Ia4.001–Ia4.180, which differ from the corresponding compounds Ia1.001–Ia1.180 by the fact that $R^{18}$ and $R^{19}$ are in each case methyl:

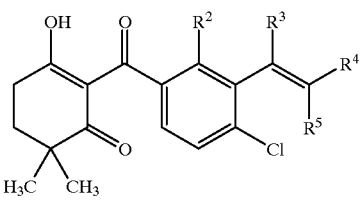

Ia4

Equally particularly extraordinarily preferred are the compounds Ia5, in particular the compounds Ia5.001–Ia5.180, which differ from the corresponding compounds Ia1.001–Ia1.180 by the fact that the $CR^{16}R^{17}$ unit is replaced by C=O:

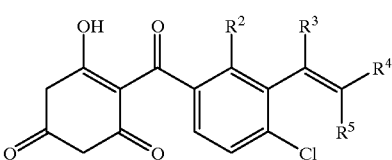

Ia5

Equally particularly extraordinarily preferred are the compounds Ia6, in particular the compounds Ia6.001–Ia6.180, which differ from the corresponding compounds Ia1.001–Ia1.180 by the fact that $R^{14}$, $R^{18}$ and $R^{19}$ are in each case methyl and the $CR^{16}R^{17}$ unit is replaced by C=O:

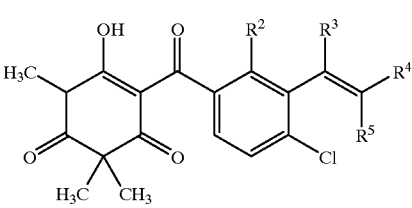

Ia6

Equally particularly extraordinarily preferred are the compounds Ia7, in particular the compounds Ia7.001–Ia7.180, which differ from the corresponding compounds Ia1.001–Ia1.180 by the fact that $R^{14}$, $R^{15}$, $R^{18}$ and $R^{19}$ are in each case methyl and the $CR^{16}R^{17}$ unit is replaced by C=O:

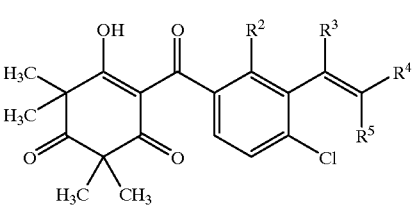

Ia7

Equally particularly extraordinarily preferred are the compounds Ia8, in particular the compounds Ia8.001–Ia8.180, which differ from the corresponding compounds Ia1.001–Ia1.180 by the fact that $R^1$ is nitro:

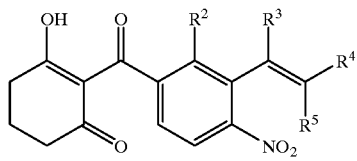
Ia8

Equally particularly extraordinarily preferred are the compounds Ia9, in particular the compounds Ia9.001–Ia9.180, which differ from the corresponding compounds Ia1.001–Ia1.180 by the fact that $R^1$ is nitro and $R^{16}$ is methyl:

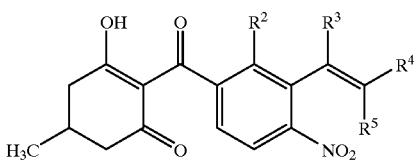
Ia9

Equally particularly extraordinarily preferred are the compounds Ia10, in particular the compounds Ia10.001–Ia10.180, which differ from the corresponding compounds Ia1.001–Ia1.180 by the fact that $R^1$ is nitro and $R^{16}$ and $R^{17}$ are in each case methyl:

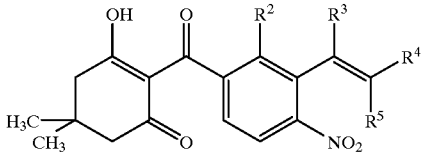
Ia10

Equally particularly extraordinarily preferred are the compounds Ia11, in particular the compounds Ia11.001–Ia11.180, which differ from the corresponding compounds Ia1.001–Ia1.180 by the fact that $R^1$ is nitro and $R^{18}$ and $R^{19}$ are in each case methyl:

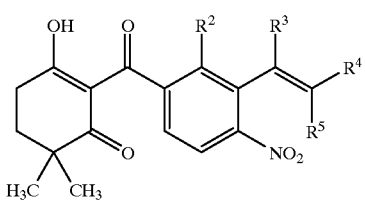
Ia11

Equally particularly extraordinarily preferred are the compounds Ia12, in particular the compounds Ia12.001–Ia12.180, which differ from the corresponding compounds Ia1.001–Ia1.180 by the fact that $R^1$ is nitro and the $CR^{16}R^{17}$ unit is replaced by C=O:

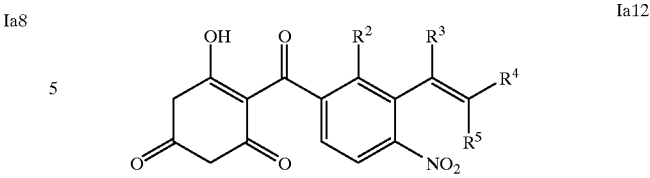
Ia12

Equally particularly extraordinarily preferred are the compounds Ia13, in particular the compounds Ia13.001–Ia13.180, which differ from the corresponding compounds Ia1.001–Ia1.180 by the fact that $R^1$ is nitro, $R^{14}$, $R^{18}$ and $R^{19}$ are in each case methyl and the $CR^{16}R^{17}$ unit is replaced by C=O:

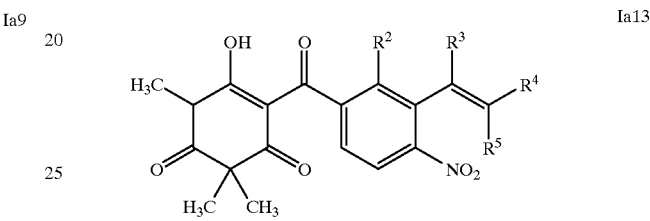
Ia13

Equally particularly extraordinarily preferred are the compounds Ia14, in particular the compounds Ia14.001–Ia14.180, which differ from the corresponding compounds Ia1.001–Ia1.180 by the fact that $R^1$ is nitro, $R^{14}$, $R^{15}$, $R^{18}$ and $R^{19}$ are in each case methyl and the $CR^{16}R^{17}$ unit is replaced by C=O:

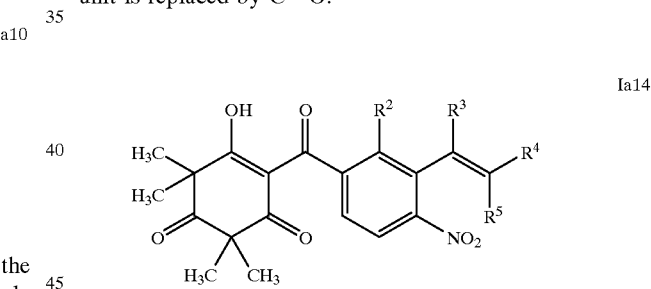
Ia14

Equally particularly extraordinarily preferred are the compounds Ia15, in particular the compounds Ia15.001–Ia15.180, which differ from the corresponding compounds Ia1.001–Ia1.180 by the fact that $R^1$ is methylsulfonyl:

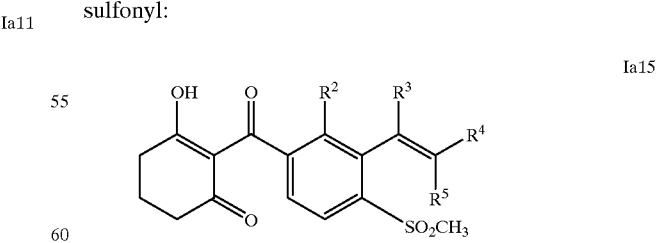
Ia15

Equally particularly extraordinarily preferred are the compounds Ia16, in particular the compounds Ia16.001–Ia16.180, which differ from the corresponding compounds Ia1.001–Ia1.180 by the fact that $R^1$ is methylsulfonyl and $R^{16}$ is methyl:

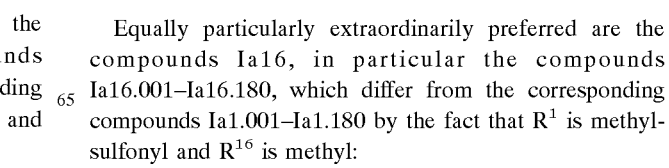

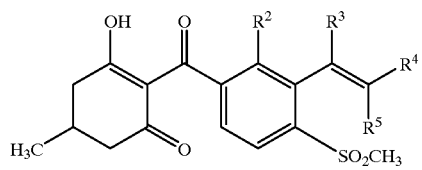
Ia16

Equally particularly extraordinarily preferred are the compounds Ia17, in particular the compounds Ia17.001–Ia17.180, which differ from the corresponding compounds Ia1.001–Ia1.180 by the fact that $R^1$ is methylsulfonyl and $R^{16}$ and $R^{17}$ are in each case methyl:

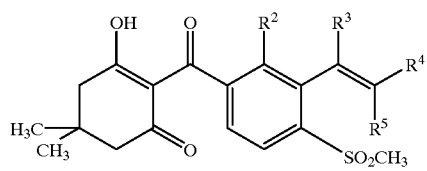
Ia17

Equally particularly extraordinarily preferred are the compounds Ia18, in particular the compounds Ia18.001–Ia18.180, which differ from the corresponding compounds Ia1.001–Ia1.180 by the fact that $R^1$ is methylsulfonyl and $R^{18}$ and $R^{19}$ are in each case methyl:

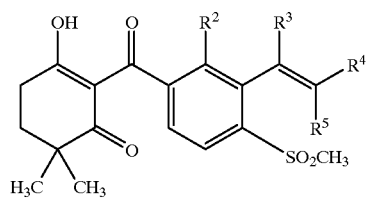
Ia18

Equally particularly extraordinarily preferred are the compounds Ia19, in particular the compounds Ia19.001–Ia19.180, which differ from the corresponding compounds Ia1.001–Ia1.180 by the fact that $R^1$ is methylsulfonyl and the $CR^{16}R^{17}$ unit is replaced by C=O:

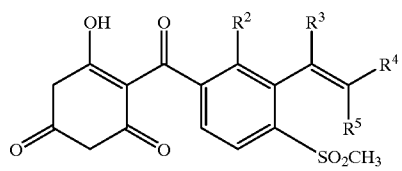
Ia19

Equally particularly extraordinarily preferred are the compounds Ia20, in particular the compounds Ia20.001–Ia20.180, which differ from the corresponding compounds Ia1.001–Ia1.180 by the fact that $R^1$ is methylsulfonyl, $R^{14}$, $R^{18}$ and $R^{19}$ are in each case methyl and the $CR^{16}R^{17}$ unit is replaced by C=O:

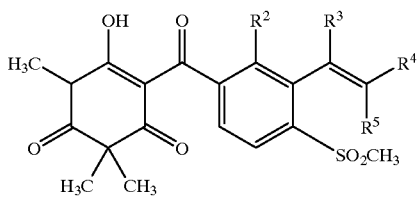
Ia20

Equally particularly extraordinarily preferred are the compounds Ia21, in particular the compounds Ia21.001–Ia21.180, which differ from the corresponding compounds Ia1.001–Ia1.180 by the fact that $R^1$ is methylsulfonyl, $R^{14}$, $R^{15}$, $R^{18}$ and $R^{19}$ are in each case methyl and the $CR^{16}R^{17}$ unit is replaced by C=O:

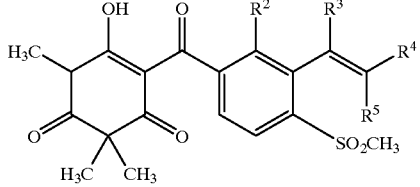
Ia21

Equally particularly extraordinarily preferred are the compounds Ia22, in particular the compounds Ia22.001–Ia22.180, which differ from the corresponding compounds Ia1.001–Ia1.180 by the fact that $R^1$ is trifluoromethyl:

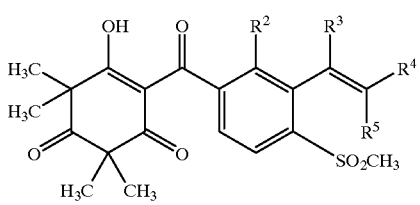
Ia22

Equally particularly extraordinarily preferred are the compounds Ia23, in particular the compounds Ia23.001–Ia23.180, which differ from the corresponding compounds Ia1.001–Ia1.180 by the fact that $R^1$ is trifluoromethyl and $R^{16}$ is methyl:

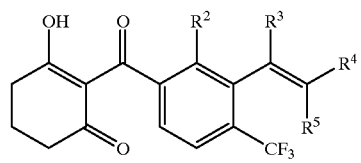
Ia23

Equally particularly extraordinarily preferred are the compounds Ia24, in particular the compounds Ia24.001–Ia24.180, which differ from the corresponding compounds Ia1.001–Ia1.180 by the fact that $R^1$ is trifluoromethyl and $R^{16}$ and $R^{17}$ are in each case methyl:

Ia24

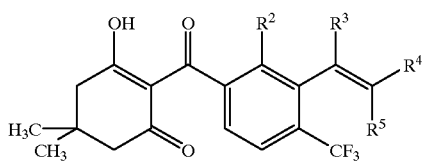

Equally particularly extraordinarily preferred are the compounds Ia25, in particular the compounds Ia25.001–Ia25.180, which differ from the corresponding compounds Ia1.001–Ia1.180 by the fact that $R^1$ is trifluoromethyl and $R^{18}$ and $R^{19}$ are in each case methyl:

Ia25

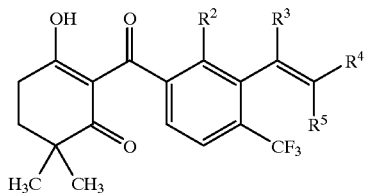

Equally particularly extraordinarily preferred are the compounds Ia26, in particular the compounds Ia26.001–Ia26.180, which differ from the corresponding compounds Ia1.001–Ia1.180 by the fact that $R^1$ is trifluormethyl and the $CR^{16}R^{17}$ unit is replaced by C=O:

Ia26

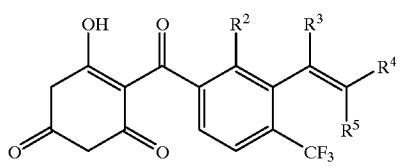

Equally particularly extraordinarily preferred are the compounds Ia27, in particular the compounds Ia27.001–Ia27.180, which differ from the corresponding compounds Ia1.001–Ia1.180 by the fact that $R^1$ is trifluoromethyl, $R^{14}$, $R^{18}$ and $R^{19}$ are in each case methyl and the $CR^{16}R^{17}$ unit is replaced by C=O:

Ia27

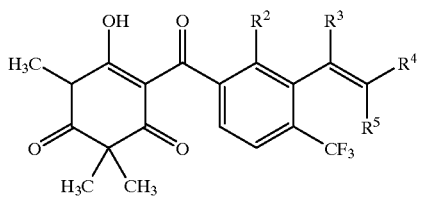

Equally particularly extraordinarily preferred are the compounds Ia28, in particular the compounds Ia28.001–Ia28.180, which differ from the corresponding compounds Ia1.001–Ia1.180 by the fact that $R^1$ is trifluoromethyl, $R^{14}$, $R^{15}$, $R^{18}$ and $R^{19}$ are in each case methyl and the $CR^{16}R^{17}$ unit is replaced by C=O:

Ia28

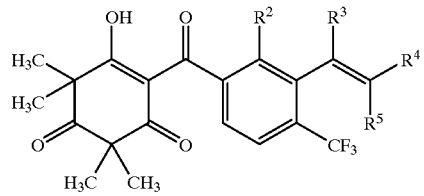

Equally particularly extraordinarily preferred are the compounds I where
- $R^1$ is halogen, such as chlorine or bromine, $C_1$–$C_6$-alkylsulfonyl such as mthylsulfonyl or ethylsulfonyl; especially preferably chlorine or methylsulfonyl;
- $R^2$ is halogen, such as chlorine or bromine; especially preferably chlorine;
- $R^3$ is hydrogen;
- $R^4$ is hydrogen, cyano, $C_1$–$C_6$-alkyl such as methyl, ethyl, propyl, 2-methylethyl, butyl or pentyl, $C_1$–$C_6$-alkoxy such as methoxy, ethoxy, $C_1$–$C_6$-alkylthio such as methylthio or ethylthio, formyl, $C_1$–$C_6$-alkylcarbonyl such as methylcarbonyl or ethylcarbonyl, $C_1$–$C_6$-alkoxycarbonyl such as methoxycarbonyl or ethoxycarbonyl, —C($R^{12}$)=N$R^{13}$; heterocyclyl, heterocycl-$C_1$–$C_4$-alkyl, phenyl, hetaryl, it being possible for the four last-mentioned radicals, in turn, to be substituted by one to three halogen atoms and/or two to three radicals selected from amongst the following group: nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylcarbonyl, $C_1$–$C_4$-alkoxycarbonyl, in particular $C_1$–$C_4$-alkyl; especially preferably hydrogen, cyano, methyl, 2-methylethyl, pentyl, methoxy, methylthio, formyl, methylcarbonyl, ethoxycarbonyl, —C($R^{12}$)=N$R^{13}$, 2-methyl-1,3-dioxolan-4-yl, 2,2-dimethyl-1,3-dioxolan-4-yl, 1,3-dioxan-2-yl, 1,3-dioxan-2-ylmethyl, phenyl, 2-furyl, 3-furyl, 2-thienyl, 3-thienyl;
- $R^5$ is hydrogen, halogen such as chlorine or bromine, or $C_1$–$C_6$-alkoxy such as methoxy or ethoxy; especially preferably hydrogen, chlorine or ethoxy;
- $R^{12}$ is hydrogen, $C_1$–$C_6$-alkyl such as methyl or ethyl, or $C_1$–$C_6$-alkoxycarbonyl such as methoxycarbonyl or ethoxycarbonyl; especially preferably hydrogen, methyl or methoxycarbonyl;
- $R^{14}$, $R^{15}$, $R^{16}$, $R^{17}$, $R^{18}$ and $R^{19}$ are hydrogen or $C_1$–$C_4$-alkyl such as methyl or ethyl; especially preferably hydrogen or methyl;
- or the $CR^{16}R^{17}$ unit can be replaced by C=O.

The 2-(3-alkenylbenzoyl)cyclohexane-1,3-diones of the formula I can be obtained by various routes, for example by the following process:

Reaction of cyclohexanediones of the formula II with an activated carboxylic acid IIIα or a carboxylic acid IIIβ which is preferably activated in situ, to give the acylation product IV, followed by a rearrangement reaction.

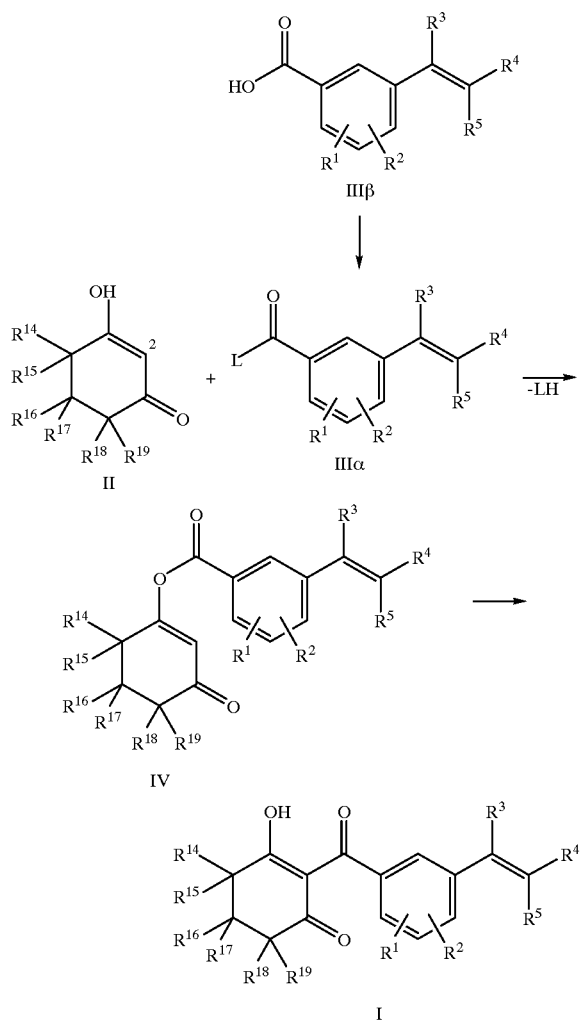

L is a nucleophilically displaceable leaving group, such as halogen, eg. bromine, chlorine, hetaryl, eg. imidazolyl, pyridyl, carboxylate, eg. acetate, trifluoroacetate, and the like.

The activated carboxylic acid can be employed directly, as in the case of the carboxylic acid halides, or be prepared in situ, for example with dicyclohexylcarbodiimide, triphenylphosphine/azodicarboxylic ester, 2-pyridine disulfide/triphenylphosphine, carbonyldiimidazole and the like.

If appropriate, it may be advantageous to carry out the acylation reaction in the presence of a base. The reactants and the auxiliary base are expediently employed in equimolar amounts. Under certain circumstances, a small excess of the auxiliary base, for example 1.2 to 1.5 mole equivalents, based on II, may be advantageous.

Suitable auxiliary bases are tertiary alkylamines, pyridine or alkali metal carbonates. Examples of solvents which can be used are chlorinated hydrocarbons such as methylene chloride, 1,2-dichloroethane, aromatic hydrocarbons such as toluene, xylene, chlorobenzene, ethers such as diethyl ether, methyl tert-butyl ether, tetrahydrofuran, dioxane, polar aprotic solvents such as acetonitrile, dimethylformamide, dimethyl sulfoxide, or esters such as ethyl acetate, or mixtures of these.

If carboxylic acid halides are employed as activated carboxylic acid component, it may be advantageous to cool the reaction mixture to 0–10° C. when adding this reactant. The mixture is subsequently stirred at 20–100° C., preferably at 25–50° C., until the reaction is complete. Work-up is carried out in the customary manner, for example the reaction mixture is poured into water and the product of value extracted. Solvents which are especially suitable for this purpose are methylene chloride, diethyl ether and ethyl acetate. After the organic phase has been dried and the solvent removed, the crude enol ester of the formula IV is purified, preferably by chromatography. However, it is also possible to employ the crude enol ester of the formula IV in the rearrangement reaction without further purification.

Rearrangement of the enol esters of the formula IV to give the compounds of the formula I is expediently carried out at from 20 to 40° C. in a solvent and in the presence of an auxiliary base, with or without the aid of a cyano compound as catalyst.

Examples of solvents which may be used are acetonitrile, methylene chloride, 1,2-dichloroethane, ethyl acetate, toluene, or mixtures of these. The preferred solvent is acetonitrile.

Suitable auxiliary bases are tertiary amines such as triethylamine, pyridine or alkali metal carbonates, such as sodium carbonate or potassium carbonate, which are preferably employed in an equimolar amount or up to a four-fold excess, based on the enol ester. Triethylamine is preferably used, by preference in twice the equimolar ratio based on the enol ester.

Suitable "rearrangement catalysts" are inorganic cyanides such as sodium cyanide or potassium cyanide and organic cyano compounds such as acetone cyanohydrin or trimethylsilyl cyanide. Normally, they are employed in an amount of from 1 to 50 mol percent based on the enol ester. Substances which are preferably employed are acetone cyanohydrin or trimethylsilyl cyanide, for example in an amount of from 5 to 15, preferably 10, mol percent based on the enol ester.

Work-up can be effected in a manner known per se. For example, the reaction mixture is acidified with dilute mineral acid, eg. 5% strength hydrochloric acid or sulfuric acid, and extracted ith an organic solvent, eg. methylene chloride or ethyl acetate. The organic extract can be extracted with 5–10% strength alkali metal carbonate solution, eg. sodium carbonate or potassium carbonate solution. The aqueous phase is acidified, and the precipitate which forms is filtered off with suction and/or extracted with methylene chloride or ethyl acetate, dried and concentrated.

(Examples of the synthesis of enol esters from cyclohexane-1,3-diones and of the cyanide-catalyzed rearrangement of the enol esters are mentioned for example in EP-A 186 118, U.S. Pat. No. 4 780 127).

The cyclohexane-1,3-diones of the formula II which are used as starting materials and which are not already known can be prepared by processes known per se (eg. EP-A 71 707, EP-A 142 741, EP-A 243 313, U.S. Pat. No. 4 249 937; WO 92/13821).

The activated carboxylic acids IIIα which are not prepared in situ can be synthesized in a manner known per se. For example, carboxylic acid halides of the formula IIIα (where L=halogen) can be synthesized by methods similar to those known from the literature (cf. L. G. Fieser, M. Fieser "Reagents for Organic Synthesis", Vol. I, pp. 767–769 (1967)) by reacting benzoic acids of the formula IIIβ with halogenating reagents such as thionyl chloride, thionyl bromide, phosgene, diphosgene, triphosgene, oxalyl chloride or oxalyl bromide.

The 3-alkenylbenzoic acids of the formula IIIβ are known from the literature or can be obtained by methods similar to those known from the literature, inter alia by hydrolyzing the corresponding 3-alkenylbenzoic esters (where M=C$_1$–C$_6$-alkoxy) of the formula IIIγ.

The 3-alkenylbenzoic esters (where M=C$_1$–C$_6$-alkoxy) of the formula IIIγ are also known from the literature or can be obtained by various routes, for example by the following processes:

A)

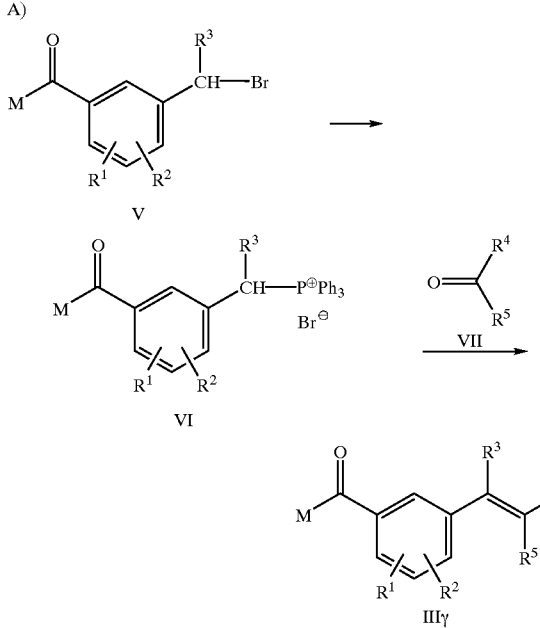

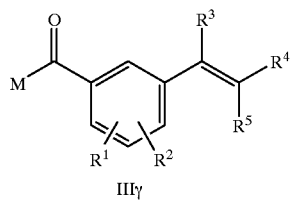

IIIγ

The compounds of the formula IIIγ can also be obtained by subjecting aldehydes or ketones of the formula VIII to a Wittig reaction or Horner-Emmons reaction with phosphonium salts IXa (see also A) or phosphonates IXb (J. March, "Advanced Organic Chemistry", 3rd ed., p. 867 et seq., Wiley-Interscience Publication, 1985).

The compounds of the formula VIII are accessible in a manner known per se by oxidizing bromine compounds of the formula V (J. March, "Advanced Organic Chemistry", 3rd ed., p. 1105 et seq., Wiley-Interscience Publication, 1985).

C)

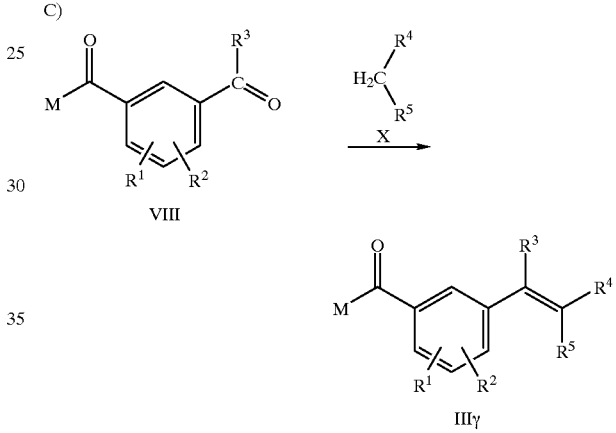

The compounds of the formula IIIγ can be obtained by subjecting phosphonium salts of the formula VI to a Wittig reaction with aldehydes or ketones (VII) in a manner known per se (J. March, "Advanced Organic Chemistry", 3rd ed., p. 864 et seq., Wiley-Interscience Publication, 1985).

The phosphonium salts of the formula VI are accessible from the bromine compounds of the formula V in a manner known per se (J. March, "Advanced Organic Chemistry", 3rd ed., p. 377 et seq., Wiley-Interscience Publication, 1985).

B)

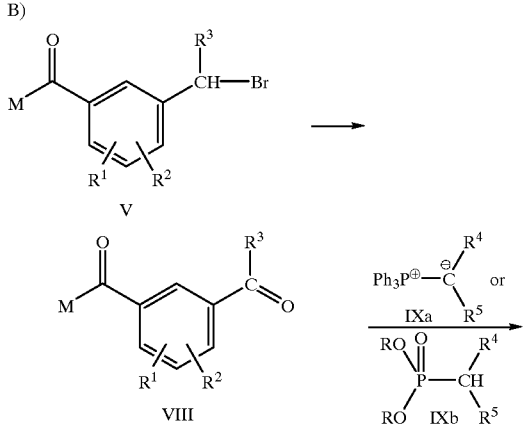

The compounds of the formula IIIγ can also be obtained in a manner known per se by subjecting aldehydes or ketones of the formula VIII to an aldol condensation reaction and related reactions (J. March, "Advanced Organic Chemistry", 3rd ed., p. 849 et seq., Wiley-Interscience Publication, 1985).

PREPARATION EXAMPLES

2-[2',4'-Dichloro-3'-(prop-1"-en-1"-yl)benzoyl]-1,3-cyclo-hexanedione (Compound 2.1)

17 g (16 mmol) of cyclohexanedione and 2.2 ml (16 mmol) of triethylamine were added to a solution of 4.0 g (16 mmol) of 2,4-dichloro-3-(prop-1'-en-1'-yl)benzoyl chloride in 50 ml of acetonitrile. After the mixture had been stirred for 12 hours at room temperature, it was poured into 500 ml of water and extracted three times with ethyl acetate. After the mixture had been dried over sodium sulfate, the solvent was removed in vacuo and the residue was purified by chromatography on silica gel (cyclohexane/ethyl acetate=9/1). The resulting enol ester was dissolved in 100 ml of acetonitrile and the solution was treated with 1.0 g (10 mmol) of trimethylsilyl cyanide and 1.3 ml of triethylamine. After the mixture had been stirred for 12 hours at room temperature, it was concentrated in vacuo, and the residue was poured into 200 ml of 10% strength sodium carbonate solution. Then, the mixture was extracted once with methyl t-butyl ether, and the aqueous phase was brought to pH 3 using 10% strength hydrochloric acid. After the mixture had been extracted with ethyl acetate and dried over sodium sulfate, the solvent was removed in vacuo. 0.6 g of a pale yellow powder of m.p. 115–120° C. remain. $^1$H NMR (CDCl$_3$/δ in ppm): 17.0 (1H); 7.45 (1H); 6.95 (1H); 6.30 (1H); 6.15 (1H); 2.75 (2H); 2.45 (2H); 2.05 (2H); 1.90 (3H).

2-[2',4'-Dichloro-3'-(2"-methoxyethen-1"-yl)benzoyl]-1,3-cyclohexanedione (Compound 2.7)

2.5 g (10 mmol) of 2,4-dichloro-3-(2'-methoxyethen-1'-yl)benzoic acid were suspended in 50 ml of acetonitrile under nitrogen and the suspension was treated with 11 g (10 mmol) of cyclohexanedione and 2.1 g (10 mmol) of dicyclohexylcarbodiimide. After the mixture had been stirred for 12 hours at room temperature, the urea which had precipitated was filtered off with suction and the solvent was removed in vacuo. The residue was purified by chromatography on silica gel (cyclohexane/ethyl acetate=9/1). The resulting enol ester was dissolved in 50 ml of acetonitrile and the solution was treated with 0.4 g (4.4 mmol) of trimethylsilyl cyanide and 0.4 g (4.4 mmol) of triethylamine. After the mixture had been stirred for 3 hours at room temperature, it was concentrated to one third of its volume and poured into 200 ml of 5% strength sodium carbonate solution. The mixture was subsequently extracted once with a small amount of methyl t-butyl ether and brought to pH 3 using 10% strength hydrochloric acid. After extraction with ethyl acetate and concentration in vacuo, 1.0 g of a yellow resin remained. $^1$H NMR (CDCl$_3$/δ in ppm): 17.0 (1H); 7.35 (1H); 7.10 (1H); 6.90 (1H); 5.80 (1H); 3.75 (3H); 2.80 (2H); 2.40 (2H); 2.05 (2H).

In addition to the 2-(3-alkenylbenzoyl)cyclohexane-1,3-diones of the formula I which have been described above, others which were prepared in a similar manner are listed in Table 2 which follows:

TABLE 2

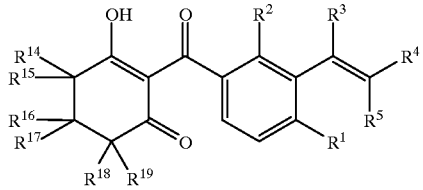

I

| No. | $R^1$ | $R^2$ | $R^3$ | $R^4$ | $R^5$ | $R^{14}$ | $R^{15}$ | $R^{16}$ | $R^{17}$ | $R^{18}$ | $R^{19}$ | Physical data m.p.[° C.]; $^1$H NMR [ppm] |
|---|---|---|---|---|---|---|---|---|---|---|---|---|
| 2.1 | Cl | Cl | H | CH$_3$ | H | H | H | H | H | H | H | 115–120 |
| 2.2 | Cl | Cl | H | phenyl | H | H | H | H | H | H | H | 17.0(1H); 7.6–7.0(9H); 2.75(2H); 2.45(2H); 2.05(2H) |
| 2.3 | Cl | Cl | H | 3-furyl | H | H | H | H | H | H | H | 77–107 |
| 2.4 | Cl | Cl | H | 2-thienyl | H | H | H | H | H | H | H | 67–77 |
| 2.5 | Cl | Cl | H | COOC$_2$H$_5$ | OC$_2$H$_5$ | H | H | H | H | H | H | 7.40(1H); 7.10(1H); 6.85(1H); 4.35(2H); 3.85(2H); 2.80(2H); 2.45(2H); 2.05(2H); 1.40(3H); 1.15(3H) |
| 2.6 | Cl | Cl | H | (1,3-dioxan-2-yl)methyl | H | H | H | H | H | H | H | oil cis/trans 35:65 |
| 2.7 | Cl | Cl | H | OCH$_3$ | H | H | H | H | H | H | H | 17.00(1H); 7.35(1H); 7.10(1H); 6.90(1H); 5.80(1H); 3.75(3H); 2.80(2H); 2.40(2H); 2.05(2H) |
| 2.8 | Cl | Cl | H | 2-furyl | H | H | H | H | H | H | H | |
| 2.9 | Cl | Cl | H | 2-furyl | H | CH$_3$ | CH$_3$ | =O | | CH$_3$ | CH$_3$ | |
| 2.10 | Cl | Cl | H | 3-furyl | H | CH$_3$ | CH$_3$ | H | H | H | H | 86–106 |
| 2.11 | Cl | Cl | H | 3-thienyl | H | H | H | H | H | H | H | 17.00(1H); 7.40–7.30(4H); 7.10–6.90(3H); 2.80(2H); 2.45(2H); 2.05(2H) |
| 2.12 | Cl | Cl | H | 2-methyl-1,3-dioxolan-4-yl | H | H | H | H | H | H | H | isomer mixture |
| 2.13 | Cl | Cl | H | phenyl | H | CH$_3$ | CH$_3$ | H | H | H | H | 62–72 |
| 2.14 | Cl | Cl | H | phenyl | H | H | H | CH$_3$ | CH$_3$ | H | H | 64–74 |
| 2.15 | Cl | Cl | H | phenyl | H | H | H | CH$_3$ | H | H | H | |
| 2.16 | Cl | Cl | H | phenyl | H | CH$_3$ | CH$_3$ | =O | | CH$_3$ | CH$_3$ | 54–74 |
| 2.17 | Cl | Cl | H | 1,3-dioxan-2-yl | H | H | H | H | H | H | H | oil |
| 2.18 | Cl | Cl | H | COOC$_2$H$_5$ | Cl | H | H | H | H | H | H | 16.90(1H); 7.80(1H); 7.40 (1H); 7.10(1H); 4.40(2H); 2.80(2H); 2.50(2H), 2.05 (2H); 1.40(3H) |
| 2.19 | Cl | Cl | H | CN | H | H | H | H | H | H | H | |
| 2.20 | Cl | Cl | H | SCH$_3$ | H | H | H | H | H | H | H | |
| 2.21 | Cl | Cl | H | COCH$_3$ | H | H | H | H | H | H | H | oil |
| 2.22 | Cl | Cl | H | CHO | H | H | H | H | H | H | H | |
| 2.23 | Cl | Cl | H | C(=NOCH$_3$)CO$_2$CH$_3$ | H | H | H | H | H | H | H | 16.50(1H); 7.60(1H); |

TABLE 2-continued

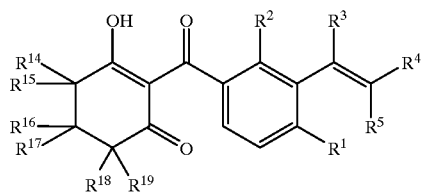

| No. | R¹ | R² | R³ | R⁴ | R⁵ | R¹⁴ | R¹⁵ | R¹⁶ | R¹⁷ | R¹⁸ | R¹⁹ | Physical data m.p.[° C.]; ¹H NMR [ppm] |
|---|---|---|---|---|---|---|---|---|---|---|---|---|
| 2.24 | Cl | Cl | H | C(=NOCH₃)CH₃ | H | H | H | H | H | H | H | 7.40(1H); 6.95(1H); 6.50(1H); 3.95(6H); 2.80(2H); 2.55(2H); 2.05(2H) 17.00(1H); 7.35(2H); 7.00 (2H); 6.85(2H); 3.95(3H); 2.55(4H); 2.05(3H); 1.95(2H) |
| 2.25 | Cl | Cl | H | C(=NOCH₃)H | H | H | H | H | H | H | H | |
| 2.26 | SO₂CH₃ | Cl | H | phenyl | H | H | H | H | H | H | H | 96–100 |
| 2.27 | SO₂CH₃ | Cl | H | phenyl | H | CH₃ | CH₃ | H | H | H | H | |
| 2.28 | SO₂CH₃ | Cl | H | phenyl | H | H | H | CH₃ | CH₃ | H | H | |
| 2.29 | SO₂CH₃ | Cl | H | phenyl | H | H | H | CH₃ | H | H | H | |
| 2.30 | SO₂CH₃ | Cl | H | phenyl | H | CH₃ | CH₃ | =O | | CH₃ | CH₃ | |
| 2.31 | Cl | Cl | H | OCH₃ | H | H | H | CH₃ | CH₃ | H | H | oil |
| 2.32 | Cl | Cl | H | CH₃ | H | CH₃ | CH₃ | H | H | H | H | resin |
| 2.33 | Cl | Cl | H | CH(CH₃)₂ | H | H | H | H | H | H | H | resin |
| 2.34 | Cl | Cl | H | CH₃ | CH₃ | H | H | H | H | H | H | resin |
| 2.35 | SO₂CH₃ | Cl | H | CH₃ | H | H | H | H | H | H | H | 63–76 |
| 2.36 | Cl | Cl | H | C(=NOCH₂phenyl)CH₃ | H | H | H | H | H | H | H | 82–122 |
| 2.37 | Cl | Cl | H | 2,2-dimethyl-1,3-dioxolan-4-yl | H | H | H | H | H | H | H | resin |
| 2.38 | Cl | Cl | H | H | H | H | H | H | H | H | H | 95–98 |
| 2.39 | Cl | Cl | H | H | H | CH₃ | CH₃ | H | H | H | H | resin |
| 2.40 | Cl | Cl | H | (CH₂)₄CH₃ | H | H | H | H | H | H | H | oil |
| 2.41 | SO₂CH₃ | Cl | H | CH₃ | H | H | H | CH₃ | H | H | H | 58 |
| 2.42 | SO₂CH₃ | Cl | H | CH₃ | H | CH₃ | CH₃ | H | H | H | H | resin |
| 2.43 | SO₂CH₃ | Cl | H | H | H | H | H | H | H | H | H | 134–135 |
| 2.44 | SO₂CH₃ | Cl | H | CH₃ | H | CH₃ | CH₃ | =O | | CH₃ | CH₃ | 76–92 |
| 2.45 | Cl | Cl | H | (CH₂)₄CH₃ | H | CH₃ | CH₃ | H | H | H | H | oil |
| 2.46 | Cl | Cl | H | C[=NOCH(CH₃)(4-Cl-phenyl)]CH₃ | H | H | H | H | H | H | H | oil |
| 2.47 | Cl | Cl | H | CH₂CH₂OH | H | H | H | H | H | H | H | |
| 2.48 | SO₂CH₃ | Cl | H | 1,3-dioxan-2-yl | H | H | H | H | H | H | H | |
| 2.49 | SO₂CH₃ | Cl | H | H | H | H | H | CH₃ | H | H | H | resin |
| 2.50 | SO₂CH₃ | Cl | H | H | H | H | H | CH₃ | CH₃ | H | H | |
| 2.51 | SO₂CH₃ | Cl | H | H | H | CH₃ | CH₃ | =O | | CH₃ | CH₃ | resin |
| 2.52 | SO₂CH₃ | Cl | H | COCH₃ | H | H | H | H | H | H | H | |
| 2.53 | SO₂CH₃ | Cl | H | OCH₃ | H | H | H | H | H | H | H | 64–74 |
| 2.54 | SO₂CH₃ | Cl | H | CN | H | H | H | H | H | H | H | 132–135 |
| 2.55 | SO₂CH₃ | Cl | H | COOC₂H₅ | H | H | H | H | H | H | H | 171–172(trans) |
| 2.56 | SO₂CH₃ | Cl | H | C(=NOCH₃)CH₃ | H | H | H | H | H | H | H | 76–77 |
| 2.57 | SO₂CH₃ | Cl | H | C(=NOCH₃)H | H | H | H | H | H | H | H | |
| 2.58 | SO₂CH₃ | Cl | H | CH₃ | H | H | H | CH₃ | CH₃ | H | H | 75–76 |
| 2.59 | Cl | Cl | H | C(=NOC₂H₅)H | H | H | H | H | H | H | H | 147–149 |
| 2.60 | SO₂CH₃ | Cl | H | COOC₂H₅ | H | H | H | H | H | H | H | 75–76(cis trans 8:2) |

The syntheses of some starting materials are described below:

2–Chloro-4-methylsulfonyl-3-(2'-phenylethen-1'-yl) benzoic Acid (Compound 3.02)

Stage a) Methyl 2-chloro-4-methylsulfonyl-3-(2'-phenylethen-1'-yl)benzoate (Compound 3.01)

10.1 g (90 mmol) of potassium tert-butoxide were added to a solution of 52.0 g (120 mmol) of benzyltriphenylphosphonium bromide in 400 ml of tetrahydrofuran. After the mixture had been stirred for 30 minutes at room temperature, 16.6 g (60 mmol) of methyl 2-chloro-3-formyl-4-methylsulfonylbenzoate in 100 ml of tetrahydrofuran were added dropwise, and stirring was continued for 3 hours at room temperature. The reaction mixture was then stirred into 500 ml of water and extracted with methyl t-butyl ether. After the solvent had been removed in vacuo, the residue was digested with diethyl ether and the triphenylphosphine oxide which had precipitated was filtered off with suction. The residue was purified by means of chromatography on silica gel (cyclohexane/ethyl acetate=95/5 to 1/1). This gave 10.9 g (52% of theory) of a pale yellow oil, which solidified slowly. ¹H NMR (CDCl₃/δ in ppm): 8.15 (1H); 7.70 (1H); 7.60–7.30 (7H); 7.00 (1H); 4.00 (3H); 3.10 (3H).

Stage b) 2–Chloro-4-methylsulfonyl-3-(2'-phenylethen-1'-yl)benzoic Acid 10.0 g (28 mmol) of methyl 2-chloro-3-(2'-phenylethen-1'-yl)-4-methylsulfonylbenzoate were dissolved in 200 ml of tetrahydrofuran/methanol (1/1) and the solution was treated with 35.2 g of 10% strength sodium hydroxide solution. The mixture was then stirred for 12 hours at room temperature and the solvent was subsequently removed in vacuo. The residue was treated with 400 ml of water and washed with ethyl acetate. The pH was then brought to 1 using 10% strength hydrochloric acid and the precipitate which had formed was filtered off with suction. After drying, 9.4 g (97% of theory) of a white powder of m.p.: 232–233° C. remained. $^1$H NMR (CDCl$_3$/δ in ppm): 8.20 (1H); 7.90 (1H); 7.55 (2H); 7.40 (4H); 7.00 (1H); 3.10 (3H).

Methyl 2,4-dichloro-3-[2'-(2''-furyl)ethen-1'-yl] benzoate (Compound 3.05)

Stage a) 2,4-Dichloro-3-methylacetophenone 235.0 g (3.0 mol) of acetyl chloride were added dropwise with stirring at 100° C. over a period of 2 hours to a solution of 502.0 g (3.12 mol) of 2,6-dichlorotoluene and 408.0 g (3.06 mol) of aluminum trichloride. After the reaction mixture had been stirred for 2 hours at 100–105° C., it was cooled and poured into 3 l of ice and 1 l of water. The solid which precipitated in the process was filtered off with suction and washed to neutrality with water. After drying at 40° C., 500.0 g of 2,4-dichloro-3-methylacetophenone were obtained as the crude product, and this was subsequently distilled under high vacuum. (B.p.: 121–128° C. (4 mbar))

Stage b) 2,4-Dichloro-3-methylbenzoic acid

First, 655.2 g (4.1 mol) of bromine and then 203.0 g (1.0 mol) of 2,4-dichloro-3-methylacetophenone in 1300 ml of 1,4-dioxane were added dropwise at 0–10° C. to a solution of 520.0 g (13 mol) of sodium hydroxide in 2600 ml of water. After the mixture had been stirred for 12 hours, the organic phase was separated off, the aqueous phase was treated with a 30% strength solution made from sodium pyrosulfite and water, and the pH was brought to 1 with hydrochloric acid. The precipitate which had precipitated out was filtered off with suction, washed with water and dried in vacuo at 60° C. This gave 197.0 g of 2,4-dichloro-3-methylbenzoic acid. (M.p.: 173–175° C.)

Stage c) Methyl 2,4-dichloro-3-methylbenzoate 60 ml of concentrated sulfuric acid were added dropwise to a solution of 424.0 g (2 mol) of 2,4-dichloro-3-methylbenzoic acid and 1500 ml of methanol. After the reaction mixture had been refluxed for 5 hours, it was cooled, concentrated in vacuo and subsequently taken up in 1000 ml of methylene chloride. The organic phase was washed with water, subsequently with 5% strength sodium hydrogen carbonate solution and then again with water, dried and concentrated in vacuo. This gave 401.0 g of methyl 2,4-dichloro-3-methylbenzoate. (B.p.: 103–107° C. (1–1.5 mbar))

Stage d) Methyl 3-bromomethyl-2,4-dichlorobenzoate 1.0 g of azobisisobutyronitrile was added to a solution of 84.0 g (0.38 mol) of methyl 2,4-dichloro-3-methylbenzoate and 67.6 g (0.38 mol) of N-bromosuccinimide in 380 ml of carbon tetrachloride. After the reaction mixture had been refluxed for 3.5 hours, it was cooled, and the precipitate which had formed was filtered off with suction. The filtrate was concentrated in vacuo and the resulting residue was extracted by stirring with methyl t-butyl ether. This gave 108.0 g of methyl 3-bromomethyl-2,4-dichlorobenzoate. (M.p.: 51–54° C.)

Stage e) (2,6-Dichloro-3-methoxycarbonyl) benzyltriphenylphosphonium bromide 80.65 g (262 mmol) of methyl 3-bromomethyl-2,4-dichlorobenzoate were dissolved in 800 ml of toluene and the solution was treated with 68.7 g (262 mmol) of triphenylphosphine. After the stirred mixture had been refluxed for 9 hours, it was cooled, and the precipitate which had formed was filtered off with suction. After drying, 129.0 g (89% of theory) of a pale beige powder remained. (M.p.: 238–239° C.)

Stage f) Methyl 2,4-dichloro-3-(2'-(2''-furyl)ethen-1'-yl) benzoate 28.0 g (50 mmol) of (2,6-dichloro-3-methoxycarbonyl) benzyltriphenylphosphonium bromide were suspended in 200 ml of tetrahydrofuran and the suspension was treated with 5.6 g (50 mmol) of potassium t-butylate at 0° C. The mixture was subsequently cooled to −20° C. and a solution of 6.2 g (65 mmol) of furfurol in 50 ml of tetrahydrofuran was added dropwise. The mixture was heated to room temperature and stirred for a further 12 hours. The reaction mixture was stirred into 200 ml of water and extracted with methyl t-butyl ether. After the solvent had been removed in vacuo, the residue was digested with diethyl ether, and the triphenylphosphine oxide which had precipitated was filtered off with suction. The residue was purified by means of chromatography on silica gel (cyclohexane/ethyl acetate= 98/2 to 90/10). This gave 8.2 g (55% of theory) of a yellow oil. $^1$H NMR (CDCl$_3$/δ in ppm): 7.55 (1H); 7.50 (1H); 7.40 (1H); 7.05 (1H); 6.95 (1H); 6.45 (2H); 3.95 (3H).

Methyl 2,4-dichloro-3-(3'-methoxycarbonyl-3'-methoxyimino-prop-1'-en-1'-yl)benzoate (Compound 3.13)

1.9 g (75 mmol) of sodium hydride were added to 17.9 g (75 mmol) of 2-methoxycarbonyl-2-methoxyiminoethyl dimethyl phosphonate in 150 ml of tetrahydrofuran and the mixture was stirred for 2 hours at room temperature. 11.7 g (50 mmol) of methyl 2,4-dichloro-3-formylbenzoate in 50 ml of tetrahydrofuran were subsequently added dropwise and the mixture was stirred for a further 12 hours at room temperature. After the reaction batch had been taken up in water, it was extracted with methyl t-butyl ether and dried, and the solvent was removed in vacuo. The residue was digested with diethyl ether and the precipitate was separated off. After drying, 11.3 g (65% of theory) of a white powder remained. (M.p.: 96–97° C.)

In addition to the compounds described above, other benzoic acid derivatives of the formula IIIa which were, or can be, prepared in a similar manner are listed in Table 3 which follows.

TABLE 3

IIIa

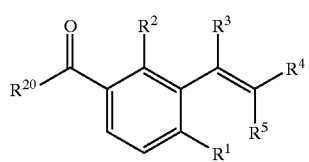

(III with $R^1$ bonded in the 4-position, $R^2$ bonded in the 2-position and $R^{20} = L^1$, OH or M)

| No. | $R^1$ | $R^2$ | $R^3$ | $R^4$ | $R^5$ | $R^{20}$ | M.p. [° C.] |
|---|---|---|---|---|---|---|---|
| 3.1 | $SO_2CH_3$ | Cl | H | phenyl | H | $OCH_3$ | 97–99 |
| 3.2 | $SO_2CH_3$ | Cl | H | phenyl | H | OH | 232–233 |
| 3.3 | Cl | Cl | H | phenyl | H | $OCH_3$ | oil |
| 3.4 | Cl | Cl | H | phenyl | H | OH | 161–166 |
| 3.5 | Cl | Cl | H | 2-furyl | H | $OCH_3$ | oil |
| 3.6 | Cl | Cl | H | 2-furyl | H | OH | 171–172 |
| 3.7 | Cl | Cl | H | $COCH_3$ | H | $OCH_3$ | 38–39 |
| 3.8 | Cl | Cl | H | $COCH_3$ | H | OH | |
| 3.9 | Cl | Cl | H | 2-thienyl | H | $OCH_3$ | oil |
| 3.10 | Cl | Cl | H | 2-thienyl | H | OH | 134–143 |
| 3.11 | Cl | Cl | H | 3-furyl | H | $OCH_3$ | 62–64 |
| 3.12 | Cl | Cl | H | 3-furyl | H | OH | 167–168 |
| 3.13 | Cl | Cl | H | $C(=NOCH_3)CO_2CH_3$ | H | $OCH_3$ | 96–97 |
| 3.14 | Cl | Cl | H | $C(=NOCH_3)CO_2CH_3$ | H | OH | 161 |
| 3.15 | Cl | Cl | H | 3-thienyl | H | $OCH_3$ | oil |
| 3.16 | Cl | Cl | H | 3-thienyl | H | OH | |
| 3.17 | Cl | Cl | H | 3-isopropyl-isoxazol-5-yl | H | $OCH_3$ | oil |
| 3.18 | Cl | Cl | H | 3-isopropylisoxazol-5-yl | H | OH | |
| 3.19 | Cl | Cl | H | CN | H | $OCH_3$ | 50–53 |
| 3.20 | Cl | Cl | H | CN | H | OH | |
| 3.21 | Cl | Cl | H | $OCH_3$ | H | $OCH_3$ | 38–40 |
| 3.22 | Cl | Cl | H | $OCH_3$ | H | OH | |
| 3.23 | Cl | Cl | Cl | $COOCH_3$ | H | $OCH_3$ | oil |
| 3.24 | Cl | Cl | Cl | $COOCH_3$ | H | OH | |
| 3.25 | Cl | Cl | H | 1,3-dioxan-2-yl | H | $OCH_3$ | 51–52 |
| 3.26 | Cl | Cl | H | 1,3-dioxan-2-yl | H | OH | 93–102 |
| 3.27 | Cl | Cl | H | (1,3-dioxan-2-yl)methyl | H | $OCH_3$ | oil |
| 3.28 | Cl | Cl | H | (1,3-dioxan-2-yl)methyl | H | OH | |
| 3.29 | Cl | Cl | $OC_2H_5$ | $COOC_2H_5$ | H | $OCH_3$ | oil |
| 3.30 | Cl | Cl | $OC_2H_5$ | $COOC_2H_5$ | H | OH | |
| 3.31 | Cl | Cl | H | 2-methyl-1,3-dioxolan-4-yl | H | $OCH_3$ | oil |
| 3.32 | Cl | Cl | H | 2-methyl-1,3-dioxolan-4-yl | H | OH | |
| 3.33 | Cl | Cl | H | CHO | H | $OCH_3$ | 66–68 |
| 3.34 | Cl | Cl | H | CHO | H | OH | |
| 3.35 | Cl | Cl | H | $CH_2$—CHO | H | $OCH_3$ | oil |
| 3.36 | Cl | Cl | H | $CH_2$—CHO | H | OH | |

The 2-(3-alkenylbenzoyl)cyclohexane-1,3-diones of the formula I and their agriculturally useful salts are suitable as herbicides, both in the form of isomer mixtures and in the form of the pure isomers. The herbicidal compositions comprising compounds of the formula I effect very good control of vegetation on non-crop areas, especially at high rates of application. In crops such as heat, rice, maize, soya beans and cotton, they act against road-leaved weeds and grass weeds without damaging the crop plants substantially. This effect is observed especially at low rates of application.

Depending on the application method in question, the compounds of the formula I, or compositions comprising them, can additionally be employed in a further number of crop plants for eliminating undesirable plants. Examples of suitable crops are the following:

Allium cepa, Ananas comosus, Arachis hypogaea, Asparagus officinalis, Beta vulgaris spec. altissima, Beta vulgaris spec. rapa, Brassica napus var. napus, Brassica napus var. napobrassica, Brassica rapa var. silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spec., Manihot esculenta, Medicago sativa, Musa spec., Nicotiana tabacum (N.rustica), Olea europaea, Oryza sativa, Phaseolus lunatus, Phaseolus vulgaris, Picea abies, Pinus spec., Pisum sativum, Prunus avium, Prunus persica, Pyrus communis, Ribes sylvestre, Ricinus communis, Saccharum officinarum, Secale cereale, Solanum tuberosum, Sorghum bicolor (s. vulgare), Theobroma cacao, Trifolium pratense, Triticum aestivum, Triticum durum, Vicia faba, Vitis vinifera and Zea mays.

Moreover, the compounds of the formula I can also be used in crops which tolerate the action of herbicides due to breeding, including genetic engineering methods.

The compounds of the formula I, or the herbicidal compositions comprising them, can be employed, for example, in the form of directly sprayable aqueous solutions, powders, suspensions, also highly-concentrated aqueous, oily or other suspensions or dispersions, emulsions, oil dispersions, pastes, dusts, materials for spreading or granules, by means of spraying, atomizing, dusting, spreading or pouring. The use forms depend on the intended purposes; in any case, they should guarantee the finest possible distribution of the active ingredients according to the invention.

The herbicidal compositions comprise a herbicidally active amount of at least one compound of the formula I or of an agriculturally useful salt of I and auxiliaries conventionally used for the formulation of crop protection products.

Suitable inert additives are essentially: mineral oil fractions of medium to high boiling point such as kerosene and diesel oil, furthermore coal tar oils and oils of vegetable or animal origin, aliphatic, cyclic and aromatic hydrocarbons, eg. paraffin, tetrahydronaphthalene, alkylated naphthalenes and their derivatives, alkylated benzenes and their derivatives, alcohols such as methanol, ethanol, propanol, butanol, cyclohexanol, ketones such as cyclohexanone, or strongly polar solvents, eg. amines such as N-methylpyrrolidone or water.

Aqueous use forms can be prepared from emulsion concentrates, suspensions, pastes, wettable powders or water-dispersible granules by adding water. To prepare emulsions, pastes or oil dispersions, the 2-(3-alkenylbenzoyl)cyclohexane-1,3-diones, as such or dissolved in an oil or solvent, can be homogenized in water by means of wetting agent, tackifier, dispersant or emulsifier. However, it is also possible to prepare concentrates composed of active substance, wetting agent, tackifier, dispersant or emulsifier and, if appropriate, solvent or oil, and these concentrates are suitable for dilution with water.

Suitable surfactants are the alkali metal, alkaline earth metal and ammonium salts of aromatic sulfonic acids, eg. ligno-, phenol-, naphthalene- and dibutylnaphthalenesulfonic acid, and of fatty acids, of alkyl- and alkylaryl sulfonates, of alkyl sulfates, lauryl ether sulfates and fatty alcohol sulfates, and salts of sulfated hexa-, hepta- and octadecanols, and of fatty alcohol glycol ether, condensates of sulfonated naphthalene and its derivatives with formaldehyde, condensates of naphthalene, or of the naphthalenesulfonic acids, with phenol and formaldehyde, polyoxyethylene octylphenyl ether, ethoxylated isooctyl-, octyl- or nonylphenol, alkylphenyl and tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or concomitantly grinding the active substances with a solid carrier. Granules, eg. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas and products of vegetable origin such as cereal meal, tree bark meal, wood meal and nutshell meal, cellulose powders or other solid carriers.

The concentrations of the compounds of the formula I in the ready-to-use products can be varied within wide ranges. In general, the formulations comprise from 0.001 to 98% by weight, preferably 0.01 to 95% by weight, of at least one active ingredient. The active ingredients are employed in a purity of from 90% to 100%, preferably 95% to 100% (according to NMR spectrum).

The compounds I according to the invention can be formulated for example as follows:

I. 20 parts by weight of the compound No. 2.2 are dissolved in a mixture composed of 80 parts by weight of alkylated benzene, 10 parts by weight of the adduct of 8 to 10 mol of ethylene oxide and 1 mol of oleic acid N-monoethanolamide, 5 parts by weight of calcium dodecylbenzenesulfonate and 5 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

II. 20 parts by weight of the compound No. 2.3 are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

III. 20 parts by weight of the active ingredient No. 2.4 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

IV. 20 parts by weight of the active ingredient No. 2.5 are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel and the mixture is ground in a hammer mill. Finely distributing the mixture in 20,000 parts by weight of water gives a spray mixture which comprises 0.1% by weight of the active ingredient.

V. 3 parts by weight of the active ingredient No. 2.1 are mixed with 97 parts by weight of finely divided kaolin. This gives a dust which comprises 3% by weight of the active ingredient.

VI. 20 parts by weight of the active ingredient No. 2.6 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the compound No. 2.11 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the compound No. 2.23 is dissolved in a mixture composed of 80 parts by weight of cyclohexanone and 20 parts by weight of Wettol® EM 31 (non-ionic emulsifier based on ethoxylated castor oil). This gives a stable emulsion concentrate.

The active ingredients of the formula I or the herbicidal compositions can be applied pre- or post-emergence. If the active ingredients are less well tolerated by certain crop plants, application techniques may be used in which the herbicidal compositions are sprayed, with the aid of the spray apparatus, in such a way that they come into as little contact as possible, if any, with the leaves of the sensitive crop plants while the active ingredients reach the leaves of undesired plants which grow underneath, or the bare soil (post-directed, lay-by).

To widen the spectrum of action and to achieve synergistic effects, the compounds of the formula I can be mixed and applied jointly with a large number of representatives of other groups of herbicidally or growth-regulatory active ingredients. Suitable components in mixtures are, for example, 1,2,4-thiadiazoles, 1,3,4-thiadiazoles, amides, aminophosphoric acid and its derivatives, aminotriazoles, anilides, aryloxy-/hetaryloxyalkanoic acids and their derivatives, benzoic acid and its derivatives, benzothiadiazinones, 2-(aroyl/hetaroyl)-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- or hetaryloxyphenoxypropionic esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

Moreover, it may be advantageous to apply the compounds of the formula I, alone or in combination with other herbicides, in the form of a mixture with additional other crop protection agents, for example with pesticides or agents for controlling phytopathogenic fungi or bacteria. Also of interest is the miscibility with mineral salt solutions which are employed for treating nutritional and trace element deficiencies. Non-phytotoxic oils and oil concentrates can also be added.

Depending on the intended aim of the control measures, the season, the target plants and the growth stage, the application rates of active ingredient are from 0.001 to 3.0, preferably 0.01 to 1.0 kg/ha active substance (a.s.)

USE EXAMPLES

The herbicidal action of the 2-(3-alkenylbenzoyl) cyclohexane-1,3-diones of the formula I was demonstrated by greenhouse experiments:

The culture containers used were plastic flowerpots containing loamy sand with approximately 3.0% of humus as substrate. The seeds of the test plants were sown separately for each species.

For pre-emergence treatment, the active ingredients, suspended or emulsified in water, were applied directly after sowing by means of finely distributing nozzles. The containers were irrigated gently to promote germination and growth and subsequently covered with translucent plastic hoods until the plants had rooted. This cover caused uniform germination of the test plants unless this was adversely affected by the active ingredients.

For the purposes of post-emergence treatment, the test plants were grown to a plant height of from 3 to 15 cm, depending on the plant habit, and only then treated with the active ingredients which had been suspended or emulsified in water. To this end, the test plants were either sown directly and grown in the same containers, or they were first grown separately as seedlings and transplanted into the test containers a few days prior to treatment. The rate of application for the post-emergence treatment was 0.5 or 0.25 kg/ha a.s.

Depending on the species, the plants were kept at from 10–25° C. and 20–35° C., respectively. The test period extended over 2 to 4 weeks. During this time, the plants were tended, and their response to the individual treatments was evaluated.

Evaluation was carried out using a scale of from 0 to 100. 100 means no emergence of the plants, or complete destruction of at least the aerial parts, and 0 means no damage or normal course of growth.

The plants used in the greenhouse experiments belonged to the following species:

| Scientific name | Common name |
| --- | --- |
| Chenopodium album | lambsquarters (goosefoot) |
| Polygonum persicaria | ladysthumb |
| Sinapis alba | white mustard |
| Solanum nigrum | black nightshade |

Compound 2.1, applied post-emergence at rates of application of 0.5 or 0.25 kg/ha a.s., effects very good control of the abovementioned weeds.

We claim:

1. A 2-(3-alkenylbenzoyl)cyclohexane-1,3-dione of the formula I

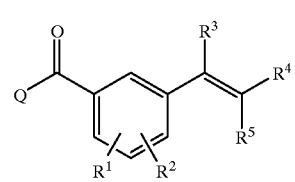

where the variables have the following meanings:
$R^1$, $R^2$ are hydrogen, nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^6$, —$OCOR^7$, —$OSO_2R^7$, —SH, —$S(O)_nR^8$, —$SO_2OR^6$, —$SO_2NR^6R^9$, —$NR^9SO_2R^7$ or —$NR^9COR^7$;

$R^3$ is hydrogen, halogen, $C_1$–$C_6$-alkyl, $C_1$–$C_6$-haloalkyl, $C_1$–$C_6$-alkoxy, $C_2$–$C_6$-alkenyl, $C_2$–$C_6$-alkynyl;

$R^4$, $R^5$ are hydrogen, nitro, halogen, cyano, thiocyanato, $C_1$–$C_6$-alkyl, $C_1$–$C_6$-haloalkyl, $C_3$–$C_6$-cycloalkyl, $C_2$–$C_6$-alkenyl, $C_4$–$C_6$-cycloalkenyl, $C_2$–$C_6$-alkynyl, $C_1$–$C_6$-alkoxy, $C_1$–$C_6$-alkylthio, $C_1$–$C_6$-haloalkoxy, —$COR^{10}$, —$CO_2R^{10}$, —$COSR^{10}$, —$CONR^{10}R^{11}$, —$C(R^{12})$=$NR^{13}$, —$PO(OR^{10})(OR^{11})$, $C_1$–$C_4$-alkyl which has attached to it a radical from amongst the following group: —$COR^{10}$, —$CO_2R^{10}$, —$COSR^{10}$, —$CONR^{10}R^{11}$ or —$C(R^{12})$=$NR^{13}$; heterocyclyl, heterocyclyl-$C_1$–$C_4$-alkyl, phenyl, phenyl-$C_1$–$C_4$-alkyl, hetaryl, hetaryl-$C_1$–$C_4$-alkyl, it being possible for the six last-mentioned radicals, in turn, to be substituted by one to three halogen atoms and/or one to three radicals from amongst the following group: nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylcarbonyl, $C_1$–$C_4$-alkoxycarbonyl; or $R^4$ and $R^5$ together form a $C_2$–$C_6$-alkanediyl chain which can be optionally mono- to tetrasubstituted by $C_1$–$C_4$-alkyl and/or can be optionally interrupted by oxygen or sulfur or by a nitrogen which is unsubstituted or substituted by $C_1$–$C_4$-alkyl;

n is 0, 1 or 2;

$R^6$ is hydrogen, $C_1$–$C_6$-alkyl, $C_1$–$C_6$-haloalkyl, $C_1$–$C_6$-alkoxy-$C_2$–$C_6$-alkyl, $C_3$–$C_6$-alkenyl or $C_3$–$C_6$-alkynyl;

$R^7$ is $C_1$–$C_6$-alkyl or $C_1$–$C_6$-haloalkyl;

$R^8$ is $C_1$–$C_6$-alkyl, $C_1$–$C_6$-haloalkyl, $C_1$–$C_6$-alkoxy-$C_2$–$C_6$-alkyl, $C_3$–$C_6$-alkenyl or $C_3$–$C_6$-alkynyl;

$R^9$ is hydrogen or $C_1$–$C_6$-alkyl;

$R^{10}$ is hydrogen, $C_1$–$C_6$-alkyl, $C_3$–$C_6$-cycloalkyl, $C_1$–$C_6$-haloalkyl, $C_3$–$C_6$-alkenyl, $C_3$–$C_6$-alkynyl, phenyl or benzyl, it being possible for the two last-mentioned radicals to be partially or fully halogenated and/or to have attached to them one to three radicals from amongst the following group: nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylcarbonyl or $C_1$–$C_4$-alkoxycarbonyl;

$R^{11}$ is hydrogen, $C_1$–$C_6$-alkyl, $C_3$–$C_6$-alkenyl or $C_3$–$C_6$-alkynyl; or $R^{10}$ and $R^{11}$ together form a $C_2$–$C_6$-alkanediyl chain which optionally can be mono- to tetrasubstituted by $C_1$–$C_4$-alkyl and/or optionally can be interrupted by oxygen or sulfur or by a nitrogen which is unsubstituted or substituted by $C_1$–$C_4$-alkyl;

$R^{12}$ is hydrogen, $C_1$–$C_6$-alkyl, $C_1$–$C_6$-haloalkyl, $C_1$–$C_6$-alkoxy, $C_1$–$C_6$-alkoxycarbonyl, $C_3$–$C_6$-cycloalkyl, $C_2$–$C_6$-alkenyl, $C_2$–$C_6$-alkynyl, phenyl or benzyl, it being possible for the two last-mentioned radicals optionally to be partially or fully halogenated and/or to have attached to them one to three radicals from amongst the following group:
nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylcarbonyl or $C_1$–$C_4$-alkoxycarbonyl;

$R^{13}$ is $C_1C_6$-alkyl, $C_1$–$C_6$-haloalkyl, $C_3$–$C_6$-cycloalkyl, $C_3$–$C_6$-alkenyl, $C_3$–$C_6$-alkynyl, $C_1$–$C_6$-alkoxy, $C_1$–$C_6$-haloalkoxy, $C_3$–$C_6$-cycloalkyloxy, $C_3$–$C_6$-alkenyloxy, $C_3$–$C_6$-alkynyloxy, phenyl, benzyl or phenyl-$C_1$–$C_4$-alkoxy, it being possible for the three last-mentioned radicals optionally to be partially or fully halogenated and/or to have attached to them one to three radicals from amongst the following group:
nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylcarbonyl or $C_1$–$C_4$-alkoxycarbonyl;

Q is a cyclohexane-1,3-dione ring of the formula II

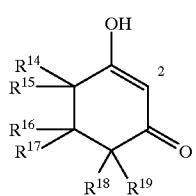

which is linked in the 2-position, where $R^{14}$, $R^{15}$, $R^{16}$, $R^{17}$, $R^{18}$ and $R^{19}$ are hydrogen or $C_1$–$C_4$-alkyl; or the $CR^{16}R^{17}$ unit may be replaced by C=O;

or an agriculturally useful salt thereof.

2. A 2-(3-alkenylbenzoyl)cyclohexane-1,3-dione of the formula I as claimed in claim 1 where $R^4$, $R^5$ are hydrogen, nitro, halogen, cyano, thiocyanato, $C_1$–$C_6$-alkyl, $C_1$–$C_6$-haloalkyl, $C_3$–$C_6$-cycloalkyl, $C_2$–$C_6$-alkenyl, $C_4$–$C_6$-cycloalkenyl, $C_2$–$C_6$-alkynyl, $C_1$–$C_6$-alkoxy, $C_1$–$C_6$-alkylthio, $C_1$–$C_6$-haloalkoxy, —$COR^{10}$, —$CO_2R^{10}$, —$COSR^{10}$, —$CONR^{10}R^{11}$, —$C(R^{12})$=$NR^{13}$, —$PO(OR^{10})(OR^{11})$, $C_1$–$C_4$-alkyl which has attached to it a radical from amongst the following group: —$COR^{10}$, —$CO_2R^{10}$, —$COSR^{10}$, —$CONR^{10}R^{11}$ or —$C(R^{12})$=$NR^{13}$; heterocyclyl, heterocyclyl-$C_1$–$C_4$-alkyl, phenyl, phenyl-$C_1$–$C_4$-alkyl, hetaryl, hetaryl-$C_1$–$C_4$-alkyl, it being possible for the six last-mentioned radicals to be substituted; by one to three halogen atoms and/or one to three radicals from amongst the following group:
nitro, cyano, $C_1$–$C_6$-alkyl, $C_1$–$C_4$-haloalkyl, $C_1$–$C_4$-alkoxy, $C_1$–$C_4$-haloalkoxy, $C_1$–$C_4$-alkylcarbonyl or $C_1$–$C_4$-alkoxycarbonyl.

or $R^4$ and $R^5$ together form a $C_2$–$C_6$-alkanediyl chain which optionally can be mono- to tetrasubstituted by $C_1$–$C_4$-alkyl and/or interrupted by oxygen or sulfur or by a nitrogen which is unsubstituted or substituted by $C_1$–$C_4$-alkyl; and $R^{13}$ is $C_1$–$C_6$-alkyl, $C_1$–$C_6$-haloalkyl, $C_3$–$C_6$-cycloalkyl, $C_3$–$C_6$-alkenyl, $C_3$–$C_6$-alkynyl, $C_1$–$C_6$-alkoxy, $C_1$–$C_6$-haloalkoxy, $C_3$–$C_6$-cycloalkoxy, $C_3$–$C_6$-alkenyloxy, $C_3$–$C_6$-alkynyloxy, phenyl, benzyl or benzyloxy, the three last-mentioned radicals optionally to be partially or fully halogenated and/or to have attached to them one to three radicals from amongst the following group:
nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylcarbonyl or $C_1$–$C_4$-alkoxycarbonyl.

3. A 2-(3-alkenylbenzoyl)cyclohexane-1,3-dione of the formula I as claimed in claim 1 where $R^1$ is nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^6$ or —$S(O)_nR^8$;

$R^2$ is hydrogen or a radical as mentioned above under $R^1$.

4. A 2-(3-alkenylbenzoyl)cyclohexane-1,3-dione of the formula I as claimed in claim 1 where $R^4$ is hydrogen, nitro, halogen, cyano, thiocyanato, $C_1$–$C_6$-alkyl, $C_1$–$C_6$-haloalkyl, $C_3$–$C_6$-cycloalkyl, $C_2$–$C_6$-alkenyl, $C_4$–$C_6$-cycloalkenyl, $C_2$–$C_6$-alkynyl, $C_1$–$C_6$-alkoxy, $C_1$–$C_6$-alkylthio, $C_1$–$C_6$-haloalkoxy, —$COR^{10}$, —$CO_2R^{10}$, —$COSR^{10}$, —$CONR^{10}R^{11}$, —$C(R^{12})$=$NR^{13}$, —$PO(OR^{10})(OR^{11})$, $C_1$–$C_4$-alkyl which has attached to it a radical from amongst the following group: —$COR^{10}$, —$CO_2R^{10}$, —$COSR^{10}$, —$CONR^{10}R^{11}$ or —$C(R^{12})$=$NR^{13}$; heterocyclyl, heterocyclyl-$C_1$–$C_4$-alkyl, phenyl, phenyl-$C_1$–$C_4$-alkyl, hetaryl, hetaryl-$C_1$–$C_4$-alkyl, it being possible for the six last-mentioned radicals to be substituted by one to three halogen atoms and/or one to three radicals from amongst the following group:
nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylcarbonyl or $C_1$–$C_4$- alkoxycarbonyl.

$R^5$ is hydrogen, halogen, cyano, thiocyanato, $C_1$–$C_6$-alkyl, $C_1$–$C_6$-haloalkyl, —$COR^{10}$, —$CO_2R^{10}$, —$COSR^{10}$, —$CONR^{10}R^{11}$ or —$PO(OR^{10})(OR^{11})$; or $R^4$ and $R^5$ together are a $C_2$–$C_6$-alkanediyl chain which can be mono- to tetrasubstituted by $C_1$–$C_4$-alkyl and/or can be interrupted by oxygen or sulfur or by a nitrogen which is unsubstituted or substituted by $C_1$–$C_4$-alkyl.

5. A 2-(3-alkenylbenzoyl)cyclohexane-1,3-dione of the formula Ia

Ia

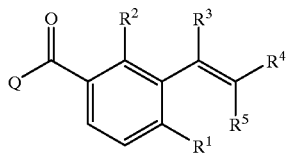

where the variables $R^1$ to $R^5$ and Q have the meanings mentioned in claim 1.

6. A process for the preparation of a 2-(3-alkenylbenzoyl) cyclohexane-1,3-dione of the formula I as claimed in any of claim 1, which comprises acylating an unsubstituted or substituted cyclohexane-1,3-dione Q with an activated carboxylic acid IIIα or with a carboxylic acid IIIβ,

IIIα

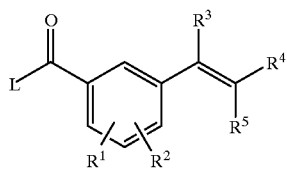

IIIβ

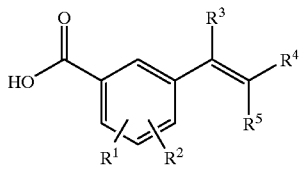

where the variables $R^1$ to $R^5$ have the meanings mentioned in claim 1 and L is a nucleophilically displaceable leaving group, and, if desired, subjecting the acylation product to a rearrangement reaction in the presence of a catalyst to give the compounds I.

7. A composition comprising a herbicidally active amount of at least one compound of the formula I or of an agriculturally useful salt of I as claimed in claim 1 and auxiliaries conventionally used for the formulation of crop protection products.

8. A process for the preparation of a herbicidally active composition as claimed in claim 7, which comprises mixing a herbicidally active amount of at least one compound of the formula I or of an agriculturally useful salt of I as claimed in claim 1 and auxiliaries conventionally used for the formulation of crop protection products.

9. A method of controlling undesired vegetation, which comprises allowing a herbicidally active amount of at least one compound of the formula I or of an agriculturally useful salt of I as claimed in claim 1 to act on plants, their environment and/or on seeds.

* * * * *